US011885917B2

(12) United States Patent
Angelsen et al.

(10) Patent No.: US 11,885,917 B2
(45) Date of Patent: *Jan. 30, 2024

(54) METHODS AND INSTRUMENTATION FOR ESTIMATION OF WAVE PROPAGATION AND SCATTERING PARAMETERS

(71) Applicant: SURF TECHNOLOGY AS, Trondheim (NO)

(72) Inventors: Bjorn A. J. Angelsen, Trondheim (NO); Johannes Kvam, Oslo (NO); Stian Solberg, Florvåg (NO)

(73) Assignee: SURF TECHNOLOGY AS, Trondheim (NO)

( * ) Notice: Subject to any disclaimer, the term of this patent is extended or adjusted under 35 U.S.C. 154(b) by 554 days.

This patent is subject to a terminal disclaimer.

(21) Appl. No.: 17/127,561

(22) Filed: Dec. 18, 2020

(65) Prior Publication Data
US 2021/0286059 A1 Sep. 16, 2021

Related U.S. Application Data

(63) Continuation-in-part of application No. 16/258,251, filed on Jan. 25, 2019, now Pat. No. 11,280,906.
(Continued)

(51) Int. Cl.
*G01S 7/52* (2006.01)
*G01S 15/89* (2006.01)
(Continued)

(52) U.S. Cl.
CPC ............ *G01S 7/52092* (2013.01); *A61B 8/13* (2013.01); *A61B 8/5269* (2013.01);
(Continued)

(58) Field of Classification Search
CPC .. G01S 15/89; G01S 15/8913; G01S 15/8927; G01S 7/52036; G01S 7/52025;
(Continued)

(56) References Cited

U.S. PATENT DOCUMENTS 6,905,465 B2  6/2005  Angelsen et al.
7,273,455 B2  9/2007  Angelsen et al.
(Continued)

FOREIGN PATENT DOCUMENTS

CN  103261909  8/2013
CN  103626269  3/2014
(Continued)

OTHER PUBLICATIONS

Hasgall PA, Di Gennaro F, Baumgartner C, Neufeld E, Gosselin MC, Payne D, Klingenböck A, Kuster N, "IT'IS Database for thermal and electromagnetic parameters of biological tissues," Version 3.0, Sep. 1, 2015, DOI: 10.13099/VIP21000-030. www.itis.ethz.ch/database https://www.itis.ethz.ch/virtual-population/tissue-properties/overview/.
(Continued)

*Primary Examiner* — Oommen Jacob
(74) *Attorney, Agent, or Firm* — Cozen O'Connor

(57) ABSTRACT

Estimation and imaging of linear and nonlinear propagation and scattering parameters in a material object where the material parameters for wave propagation and scattering has a nonlinear dependence on the wave field amplitude. The methods transmit at least two pulse complexes composed of co-propagating high frequency (HF) and low frequency (LF) pulses along at least one LF and HF transmit beam axis, where said HF pulse propagates close to the crest or trough of the LF pulse along at least one HF transmit beam, and where one of the amplitude and polarity of the LF pulse varies between at least two transmitted pulse complexes. At least one HF receive beam crosses the HF transmit beam at an angle, to provide at least two HF cross-beam receive signals from at least two transmitted pulse complexes with different LF pulses.

36 Claims, 7 Drawing Sheets

Related U.S. Application Data

(60) Provisional application No. 63/044,679, filed on Jun. 26, 2020.

(51) Int. Cl.
*A61B 8/08* (2006.01)
*A61B 8/13* (2006.01)
*A61N 7/00* (2006.01)

(52) U.S. Cl.
CPC ........ *G01S 7/5202* (2013.01); *G01S 7/52077* (2013.01); *G01S 15/8993* (2013.01); *G01S 15/8995* (2013.01); *A61N 2007/0052* (2013.01)

(58) Field of Classification Search
CPC ............. G01S 15/8929; G01S 7/52092; G01S 15/8906; G01S 7/52038; G01S 15/8952; G01S 7/5202; G01S 15/894; G01S 15/8922; A61N 2007/0073
See application file for complete search history.

(56) References Cited

U.S. PATENT DOCUMENTS

| | | | |
|---|---|---|---|
| 7,641,613 B2 | 1/2010 | Angelsen et al. | |
| 7,727,156 B2 | 6/2010 | Angelsen et al. | |
| 8,038,616 B2 | 10/2011 | Angelsen et al. | |
| 8,182,428 B2 | 5/2012 | Angelsen et al. | |
| 8,550,998 B2 | 10/2013 | Angelsen et al. | |
| 9,939,413 B2 | 4/2018 | Angelsen et al. | |
| 11,280,906 B2* | 3/2022 | Angelsen | G01S 15/8929 |
| 2005/0277835 A1 | 12/2005 | Angelsen et al. | |
| 2006/0052699 A1* | 3/2006 | Angelsen | G01S 7/52042 |
| | | | 600/437 |
| 2009/0178483 A1 | 7/2009 | Angelsen et al. | |
| 2010/0036244 A1 | 2/2010 | Angelsen et al. | |
| 2010/0249590 A1 | 9/2010 | Kanayama et al. | |
| 2012/0095699 A1* | 4/2012 | Angelsen | G01S 15/8952 |
| | | | 702/33 |
| 2013/0279294 A1* | 10/2013 | Angelsen | G01S 7/52042 |
| | | | 367/87 |
| 2014/0150556 A1 | 6/2014 | Angelsen et al. | |
| 2019/0009111 A1 | 1/2019 | Myhr et al. | |
| 2019/0235076 A1 | 8/2019 | Angelsen et al. | |
| 2021/0286059 A1* | 9/2021 | Angelsen | G01S 15/8913 |

FOREIGN PATENT DOCUMENTS

| | | |
|---|---|---|
| CN | 103869306 | 6/2014 |
| JP | 62-227332 | 10/1987 |
| WO | WO 2006/009469 | 1/2006 |

OTHER PUBLICATIONS

Hartmann B: "Potential energy effects on the sound speed in liquids" J. Acoust. Soc. Am. 65(6), Jun. 1979:1392-1396.

Kvam J, Holm S, Angelsen B: "Exploiting Balou's rule for Better Tissue Classification". Proceeding Acoust Soc Am, May 14, 2018, http://dx.doi.org(DOI number).

Hormati A, Jovanovi I, Roy O, Vetterli M: "Robust Ultrasound Travel-time Tomography Using the Bent Ray Model" Medical Imaging 2010: Ultrasonic Imgaing, Tomography, and Therapy, Ed: J D'Hooge, S A McAleavey, Proc SPIE vol. 7629, 76290I.

Li C, Duric N, Littrup P, Huang L: "In Vivo Breast Sound-Speed Imaging with Ultrasound Tomography", Ultrasound Med Biol. Oct. 2009; 35(10) 1615-1628.

Opielinski K J, Pruchnicki P, Gudra T, Podgorski P, Krasnicki T, Kurcz J, Sasiadek M: "Ultrasound Transmission Tomography Imaging of Structure of Breast Elastography Phantom Compared to US, CT, and MRI." Archives of Acoustics, vol. 38, No. 3, pp. 321-334 (2013).

Opielinski K J, Pruchnicki P, Szymanowski P, Szeoieniec W K, Szweda H, Swis E, Jozwik M, Tenderenda M, Bulkowski M: "Multimodal ultrasound computer assisted tomography: An approach to the recognition of breast lesions." Computerized Medical Imaging and Graphics 65 (2018) 102-114.

Huang L, Shin J, Chen T, Lin Y, Intrator M, Hanson K, Epstein K, Sandoval D, Williamson M: "Breast ultrasound tomography with two parallel transducer arrays: Preliminary clinical results". Medical Imaging 2015: Ultrasound Imaging and Tomography, Ed: J. G. Bosch, N Duric, Proc. of SPIE vol. 941916.

Angelsen B A J: "Ultrasound Imaging—Waves, Signal, and Signal Processing". Emantec AS, Trondheim, Norway, Apr. 30, 2000.

Notice of Allowance dated Oct. 27, 2021 issued in U.S. Appl. No. 16/717,938.

Notice of Allowance dated Nov. 12, 2021 issued in U.S. Appl. No. 16/258,251.

Office Action dated Jun. 4, 2021 issued in U.S. Appl. No. 16/258,251.

Office Action dated Jun. 25, 2021 issued in U.S. Appl. No. 16/717,938.

Myhre, "Speeding up SURF Imaging", Sep. 2013, 5 pages.

Hussain. "Evaluation of cross-beam vector Doppler ultrasound systems for accurate 3-D velocity measurements", Ultrasonics Symposium Proceedings, 2012, 162 pages.

Office Action dated Sep. 20, 2022 issued in European Patent Application No. 19712014.0.

Search Report dated Dec. 6, 2019 issued in International Patent Application No. PCT/IB2019/000085.

Hansen et al. "Nonlinear propagation delay and pulse distortion resulting from dual frequency band transmit pulse complexes", The Journal of The Acoustical Society of America, vol. 129, No. 2, Feb. 1, 2011, pp. 1117-1127.

Written Opinion dated Apr. 23, 2021 issued in International Patent Application No. PCT/IB2020/001066.

Office Action dated Mar. 26, 2021 issued in U.S. Appl. No. 16/717,938.

Jochen M. Rau et al., "Methods for Reverberation Suppression Utilizing Dual Frequency Band Imaging", The Journal Of The Acoustical Society Of America, Sep. 1, 2013, pp. 2313-2325, vol. 134, No. 3.

Office Action dated Aug. 3, 2023 issued in Chinese Patent Application No. 201980018013.2.

Decision to Grant dated Aug. 24, 2023 issued in Japanese Patent Application No. 2021-535268.

* cited by examiner

Nonlinear compression elasticity in tissues $$c(\underline{r}, p_L) = c_0(\underline{r})(1 + \beta(\underline{r})p_L) \qquad c_0(\underline{r}) = 1/\sqrt{\rho_0(\underline{r})\kappa(\underline{r})} \qquad p_L \text{ - LF pressure}$$

| | Name | $\rho_0$ kg/m³ | $c_0$ m/s² | $\kappa^a$ GPa⁻¹ | $\beta_n$ -- | $\beta$ GPa⁻¹ |
|---|---|---|---|---|---|---|
| 1 | Liver | 1060 | 1595 | 0.371 | 4.3 | 1.59 |
| 2 | Muscle, skeletal | 1050 | 1580 | 0.382 | 4.3 | 1.64 |
| 3 | Non-fatty | 1055 | 1575 | 0.382 | 4.5 | 1.71 |
| 4 | Muscle, cardiac | 1060 | 1576 | 0.38 | 4.55 | 1.73 |
| 5 | Brain | 1040 | 1560 | 0.395 | 4.55 | 1.80 |
| 6 | Kidney | 1050 | 1560 | 0.391 | 4.7 | 1.84 |
| 7 | Spleen | 1054 | 1567 | 0.386 | 4.9 | 1.89 |
| 8 | Breast Gland | 1040 | 1505 | 0.425 | 5.82 | 2.47 |
| 9 | Fatty | 985 | 1465 | 0.473 | 5.25 | 2.48 |
| 10 | Adipose | 950 | 1450 | 0.501 | 6 | 3.0 |

$^a$ Calculated as $\kappa = 1/\rho_0 c_0^2 \qquad \beta = \beta_p = \beta_n \kappa$

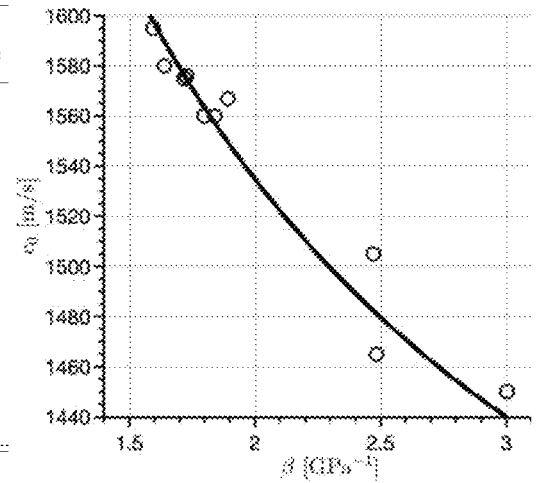

FIG. 10

METHODS AND INSTRUMENTATION FOR ESTIMATION OF WAVE PROPAGATION AND SCATTERING PARAMETERS

CROSS REFERENCE TO RELATED APPLICATIONS

This application is a continuation in part of U.S. Ser. No. 16/258,251 which claims priority from provisional application No. 62/621,952 filed on Jan. 25, 2018; provisional application No. 62/732,409 filed on Sep. 17, 2018; and provisional application No. 62/780,810 filed on Dec. 17, 2018. This application also claims priority from provisional application No. 63/044,679 filed Jun. 26, 2020. The entire content of the forgoing being incorporated by reference.

1. FIELD OF THE INVENTION

The present invention is directed to methods and instrumentation for imaging of linear and nonlinear propagation and scattering parameters of an object using transmission of dual frequency pulse complexes composed of a high frequency (HF) and low frequency (LF) pulse. Imaging with acoustic pressure waves is shown as an example, but the methods are also useful for imaging with shear elastic waves and coherent electromagnetic waves. Applications of the invention are for example, but not limited to, medical imaging and therapy, non-destructive testing, industrial and biological inspections, geological applications, SONAR and RADAR applications.

BACKGROUND OF THE INVENTION

Transmission of dual frequency pulse complexes composed of a high frequency (HF) and low frequency (LF) pulse for imaging of nonlinear propagation and scattering parameters of an object is described in US patents 1-4 (U.S. Pat. Nos. 7,641,613; 8,038,616; 8,550,998; 9,291,493). The methods also provide suppression of multiple scattering noise (reverberation noise) and improved imaging of linear and nonlinear scatterers. Imaging with coherent acoustic pressure waves is shown as an example, but it is clear that the methods are also useful for imaging with all types of coherent wave imaging, such as shear elastic waves and electromagnetic waves.

The cited methods require estimation of one or both of a nonlinear propagation delay (NPD) and a nonlinear propagation pulse form distortion (PFD) which both are challenging tasks. The present invention describes new methods and instrumentation for improved estimation of both the NPD and the PFD, and provides scatter images with reduced multiple scattering noise and images of nonlinear scatterers. Combined with measurements with zero LF pulse, the invention also provides estimates of linear propagation and scattering parameters, that combined with the estimates of nonlinear parameters is used to obtain a thermo-elastic description of the object.

SUMMARY OF THE INVENTION

This summary gives a brief overview of components of the invention and does not present any limitations as to the extent of the invention, where the invention is solely defined by the claims appended hereto.

The current invention provides methods and instrumentation for estimation and imaging of linear and nonlinear propagation and scattering parameters in a material object where the material parameters for wave propagation and scattering have a nonlinear dependence on the wave field amplitude. The methods have general application for both acoustic and shear elastic waves such as found in SONAR, seismography, medical ultrasound imaging, and ultrasound nondestructive testing, and also coherent electromagnetic waves such as found in RADAR and laser imaging. In the description below one uses acoustic waves as an example, but it is clear to anyone skilled in the art how to apply the methods to elastic shear waves and coherent electromagnetic waves.

In its broadest form the methods comprises transmitting at least two pulse complexes composed of a co-propagating high frequency (HF) and a low frequency (LF) pulse along at least one LF and HF transmit beam axis, where said HF pulse propagates close to the crest or trough of the LF pulse along at least one HF transmit beam, and where one of the amplitude and polarity of the LF pulse varies between at least two transmitted pulse complexes, where the amplitude of the LF pulse can be zero for a pulse complex and the amplitude of at least one LF pulse of said at least two transmitted pulse complexes is non-zero.

The LF pulse produces a manipulation of the propagation velocity of the co-propagating HF pulse. At the first scattering, the amplitude of the LF pulse drops so much that one can neglect the LF manipulation of the propagation velocity for the scattered signal. The LF pulse polarity and/or amplitude hence produces a modification of the HF pulse delay from transmission to reception that we call the nonlinear propagation delay (NPD) that i) accumulates with the propagation distance to the first scatterer, and ii) is proportional to the LF pulse amplitude, and iii) changes polarity with the LF pulse amplitude. Variations of the LF pulse along the HF pulse produces a pulse form distortion (PFD) that also i) accumulates with the propagation distance to the first scatterer, and ii) is proportional to the LF pulse amplitude, and iii) changes polarity with the LF pulse amplitude.

Multiple scattered HF pulses, that arrive to the receiver at the same time as $1^{st}$ order scattered HF pulses, appear in the received signal as multiple scattered noise (MSN) that often reduces ultrasound image quality, and provide challenges for clutter suppression with Doppler measurements. The drop in the amplitude of the HF pulse for each scattering implies in practice that higher than $3^{rd}$ order scattered HF pulses give negligible noise. Because the drop of the LF pulse at the first scattering, the co-propagating LF pulse produces a NPD and a PFD of the MSN given by those of the HF pulse at the $1^{st}$ scattering, and are hence different from the NPD and a PFD of the $1^{st}$ order scattered signal arriving at the same time at the HF receiver transducer.

High quality estimation of the NPD opens for suppression of multiple scattering noise and imaging of nonlinear scattering, as shown in U.S. Pat. Nos. 7,641,613; 8,038,616; 8,550,998; 9,291,493. In US Parent patent application Ser. No. 16/258,251 it is also shown that good estimates of the NPD opens for quantitative estimation of the nonlinear bulk elasticity of tissues.

For back scatter imaging, it is described in U.S. Pat. No. 9,291,493 how the MSN can be separated into two classes, Class I and Class II, with opposite paths of the scattering: The $1^{st}$ scatterer of Class I is the last scatterer of Class II, and the $1^{st}$ scatterer of Class II is the last scatterer of Class I. The NPD and PFD of the Class I and Class II MSN pulses are therefore different, and also different from the NPD and a PFD of the $1^{st}$ order scattered signal arriving at the same time. For backscatter imaging, the signal received at a given arrival time is therefore generally composed of three components: i) a $1^{st}$ order scattered signal, and ii) a Class I MSN component, and iii) a Class II MSN component, where all three components have different NPDs and PFDs. This makes estimation of the NPD and PFD from backscattered signals difficult in many practical situations.

According to the invention, and also as described in U.S. Parent patent application Ser. No. 16/258,251, it is shown that using HF receive beams that crosses the HF transmit beam gives receive signals with low MSN that produces an advantage for estimation of the NPD. The NPD at the HF cross-beam observation cell can for example be obtained by transmitting two pulse complexes along the same LF and HF beams and with opposite polarities of the LF pulse. Comparing the difference in arrival time of the HF signal from the two pulse complexes and the same HF cross-beam observation cell, for example through correlation, gives the NPD, as described in more detail below.

The HF cross-beam receive signals are processed to estimate one or both of i) a nonlinear propagation delay (NPD), and ii) a nonlinear pulse form distortion (PFD) of the transmitted HF pulse for said cross-beam observation cell, where one or both of said NPD and PFD are used in the further processing to estimate one or more of i) a local nonlinear propagation parameter, and ii) a local quantitative nonlinear propagation parameter $\beta_p$, and iii) a local value of the linear pulse propagation velocity $c_0$, and iv) a linearly scattered HF signal, and v) a nonlinearly scattered HF signal, and vi) local changes in tissue structure during therapy, and vii) local changes in tissue temperature during HIFU therapy. The spatial variations of the estimated linear propagation velocity is used for corrections of wave-front aberrations to improve focal resolution of transmit and receive beams used for the images.

In general said at least one HF receive cross-beam is focused on the HF transmit beam axis forming a cross-beam observation cell as the cross-over region of the HF transmit and HF receive cross-beams.

A local nonlinear propagation parameter can be estimated through receiving scattered signals from the HF transmitted pulse for at least two HF receive cross-beams with close distance along the HF transmit beam, and estimating a nonlinear propagation delay (NPD) of the transmitted HF pulse at the at least two cross-beam observation cells determined by the cross-over between the HF transmit beam and each of the said at least two HF receive cross-beams. Said estimated NPDs from neighboring cross-beam observation cells along a HF transmit beam are combined to form estimates of the local nonlinear propagation parameter. Scaling said estimated local nonlinear propagation parameter by an estimate of the LF pulse pressure at the location of the HF pulse gives a quantitative estimate of the nonlinear propagation parameter $\beta_p$. The estimated $\beta_p$ gives rise to an estimate of the local linear propagation velocity $c_0$, a change in tissue structure during therapy, and a change in the local tissue temperature during HIFU therapy. Both a local non-linearly and a linearly scattered signal may be obtained through correcting said at least two HF receive signals with one or both of i) the NPD, and ii) the PFD to produce two corrected signals, and combining said at least two corrected signals.

The invention further devices to also use a HF back-scatter receive beam with the same beam axis as the HF transmit beam to record HF back-scatter receive signals. The NPD and the PFDs are determined by the LF and HF transmit beams and the LF pulse polarity and the amplitude, according to Eqs.(12,13). As we are using the same LF and HF transmit beams as for the cross-beam receive signals, we get the same NPD and PFD for the back-scatter as for the cross beam receive signals. The estimated PFD and/or the NPD are processed to estimate delay and speckle/pulse form corrections of the HF back-scatter receive signals for suppression of multiple scattering noise, for example as described in U.S. Pat. Nos. 7,641,613, 8,038,616, 8,550,998, 9,291,493. For each HF back-scatter receive beams the at least two HF back-scatter signals from at least two transmitted pulse complexes with different LF pulses are corrected with the estimated delay and speckle/pulse form corrections to produce at least two corrected HF back-scatter signals that are combined to provide HF noise-suppressed back-scatter signals with suppression of multiple scattering noise, for example as described in U.S. Pat. Nos. 8,038,616, 8,550,998, 9,291,493.

2D and 3D images of the estimated parameters and signals may be obtained by scanning the transmit beam and matched HF cross-beam and HF back-scatter beams across a 2D or a 3D region of the object, and recording HF back-scatter and/or cross-beam receive signals and back-scattered signals with further processing according to the invention to produce local estimates of propagation and scattering parameters.

The size of the cross-beam observation cell may with 2D or 3D scanning be synthetically reduced through spatial filtering of the HF cross-beam receive signals from several neighboring cross-beam observation cells. In this process one can use the estimated linear propagation velocity to correct for wave front aberrations in the spatial filtering.

The invention further devices to use HF back-scatter receive beams that are equal to the HF transmit beams, and for multiple depths carry through lateral filtering of one of i) the HF back-scatter receive signals, and ii) the HF noise-suppressed back-scatter signals, to produce HF signals from combined HF transmit and receive beams that are synthetically focused for said multiple depths, for example as described in U.S. Pat. No. 9,291,493. In this process one can use the estimated linear propagation velocity to correct for wave front aberrations in the spatial filtering.

The invention also describes instruments for carrying through the practical measurements and processing according to the invention, in particular to obtain local estimates of the PFD and/or the NPD, and one or more of the parameters: i) a local nonlinear propagation parameter, and ii) a local quantitative nonlinear propagation parameter $\beta_p$, and iii) a local value of the linear pulse propagation velocity $c_0$, and iv) a linearly scattered HF signal with suppression of multiple scattering noise, and v) a nonlinearly scattered HF signal, and vi) local changes in tissue structure during therapy, and vii) local changes in tissue temperature during therapy.

With one version of the instrument, HF back-scatter and/or cross beam receive signals are generated in dedicated beam forming HW according to known methods, and digital HF receive signals are transferred to the processing structure for storage and further processing in a general SW programmable processor structure of different, known types.

In another version of the instrument the individual receiver element signals are digitized and transferred to a general SW programmable processor structure where the receive beam forming and further processing is SW programmed.

The instrument comprises a display system for display of estimated parameters and images according to known technology, and user input to the instrument according to known methods. The transmit and receive of HF and LF pulses are obtained with known transducer arrays, for example as described in U.S. Pat. Nos. 7,727,156 and 8,182,428.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

FIG. 10 Acoustic compression elasticity data for some typical tissues, showing good correlation between the nonlinear elasticity parameter $\beta_p$ and the linear propagation velocity $c_0$.

Figure 1:
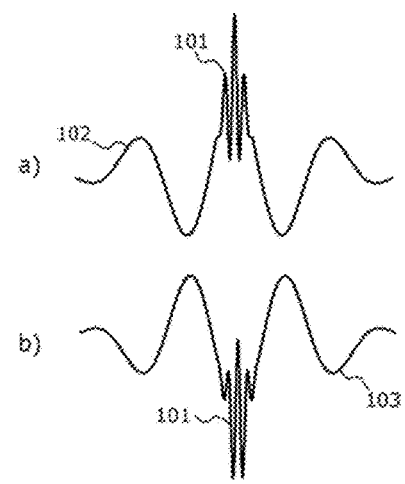
FIG. 1 shows example pulse complexes comprising a high frequency (HF) pulse and a low frequency (LF) pulse, where two typical forms of LF pulses are shown.

DETAILED DESCRIPTION OF THE PRESENTLY PREFERRED EMBODIMENTS 5.1 Theory of Nonlinear Propagation and Scattering A. Wave Equation for 2nd Order Nonlinear Bulk Elasticity For acoustic waves in fluids and solids, nonlinear bulk elasticity is commonly defined through a Taylor series expansion of the acoustic pressure to the $2^{nd}$ order in relation to the mass density as $$p = A\frac{\rho_1}{\rho_0} + \frac{B}{2}\left(\frac{\rho_1}{\rho_0}\right)^2 = A\frac{\rho_1}{\rho_0}\left(1 + \frac{B}{2A}\left(\frac{\rho_1}{\rho_0}\right)\right) \quad (1)$$

$$A = \rho_0 \left(\frac{\partial p}{\partial \rho}\right)_{0,s} = \frac{1}{\kappa}$$

$$B = \rho_0^2 \left(\frac{\partial^2 p}{\partial \rho^2}\right)_{0,s}$$

$p(\underline{r},t)$ is the instantaneous, local acoustic pressure as a function of space vector, $\underline{r}$, and time t, $\rho(\underline{r},t)=\rho_0(\underline{r},t)+\rho_1(\underline{r},t)$ is the instantaneous mass density with $\rho_0$ as the equilibrium density for p=0, $\kappa(\underline{r})$ is the isentropic compressibility, and B is a nonlinearity parameter. We use the Lagrange spatial description where the co-ordinate vector $\underline{r}$ refers to the location of the material point in the unstrained material (equilibrium), and $\underline{\psi}(\underline{r},t)$ describes the instantaneous, local displacement of a material point from its unstrained position $\underline{r}$, produced by the particle vibrations in the wave.

The term $A \cdot (\rho_1/\rho_0)$ describes linear bulk elasticity, and hence does the last term $(B/2A)(\rho_1/\rho_0)$ in the parenthesis represent deviation from linear elasticity. The parameter B/2A is therefore commonly used to describe the magnitude of nonlinear bulk elasticity.

The continuity equation in Lagrange coordinates takes the form $$-\nabla \underline{\psi} = \frac{\rho_1}{\rho} = \frac{\rho_1}{\rho_0 + \rho_1} \quad (2)$$

$$\frac{\rho_1}{\rho_0} = -\frac{\nabla \underline{\psi}}{1+\nabla \underline{\psi}} \approx -\nabla \underline{\psi}(1-\nabla \underline{\psi})$$

To the $2^{nd}$ order in $\nabla\underline{\psi}$ we then get isentropic state equation as $$p = -A\nabla\underline{\psi}(1-\nabla\underline{\psi}) + \frac{B}{2}(\nabla\underline{\psi})^2 = -\frac{1}{\kappa}\nabla\underline{\psi} + \frac{\beta_n}{\kappa}(\nabla\underline{\psi})^2 \quad (3)$$

$$\beta_n = 1 + \frac{B}{2A} = 1 + \frac{B}{2}\kappa$$

Eqs.(1, 3) describes isentropic compression, where there is no transformation of elastic energy to heat, i.e. no absorption of acoustic energy in the wave propagation. Linear absorption can be introduced by adding a temporal convolution term $h_{ab} \otimes \nabla\underline{\psi}$, where $h_{ab}$ $(\underline{r},t)$ is a convolution kernel that represents absorption of wave energy to heat due to deviation from fully isentropic compression.

For the analysis of wave propagation and scattering it is convenient to invert Eq.(3) to the $2^{nd}$ order in p and add the absorption term that gives a material equation for bulk elasticity to the $2^{nd}$ order in p $$\frac{\delta V}{\Delta V} = \frac{\rho_1}{\rho} = -\nabla\underline{\psi} = [1 - \beta_p(\underline{r})p]\kappa(\underline{r})p + h_{ab}\underset{t}{\otimes}\kappa(\underline{r})p \quad (4)$$

$$\beta_p(\underline{r}) = \beta_n(\underline{r})\kappa(\underline{r})$$

$$\beta_n(\underline{r}) = 1 + \frac{B(\underline{r})}{2A(\underline{r})} = 1 + \frac{1}{2}B(\underline{r})\kappa(\underline{r})$$

where the absorption term is small and we include only $1^{st}$ order in p. Attenuation of a propagating wave is given by both the extinction coefficient of the incident wave, which is the sum of absorption to heat given by $h_{ab}$, and scattering of the wave.

The $2^{nd}$ order approximation of Eqs.(1, 3, 4) holds for soft tissues in medical imaging, fluids and polymers in non-destructive testing, and also rocks in seismography that show special high nonlinear bulk elasticity due to their granular micro-structure. Gases generally show stronger nonlinear elasticity, where higher order terms in the pressure often might be included. Micro gas-bubbles with diameter much lower than the acoustic wavelength in fluids, show in addition a resonant compression response to an oscillating pressure which gives a differential equation (frequency dependent) form of the nonlinear elasticity, as described by the Rayleigh-Plesset equation [18].

To develop a full wave equation, we must include Newtons law of acceleration, that for waves with limited curvature of the wave-fronts can be described in the Lagrange description as $$\rho_0 \frac{\partial^2 \psi}{\partial t^2} \approx -\nabla p \quad (5)$$

$$\frac{\partial^2 \nabla \psi}{\partial t^2} = -\nabla \left(\frac{1}{\rho_0} \nabla p\right)$$

Both the mass density, the compressibility, and the absorption have spatial variation in many practical materials, like soft tissue and geologic materials. We separate the spatial variation into a slow variation that mainly influences the forward propagation of the wave (subscript a), and a rapid variation that produces scattering of the wave (subscript f), as $$\rho_0(\underline{r}) = \rho_a(\underline{r}) + \rho_f(\underline{r}) \kappa(\underline{r}) = \kappa_a(\underline{r}) + \kappa_f(\underline{r}) \beta_p(\underline{r}) = \beta_{pa}(\underline{r}) + \beta_{pf}(\underline{r}) \quad (6)$$

Combining Eqs.(4-6)), using $1/\rho_0 = \rho_a/\rho_a\rho_0 = (\rho_0-\rho_f)/\rho_a\rho_0 = 1/\rho_a - \gamma/\rho_a$, $\gamma = \rho_f/\rho_0$, produces a wave equation of a form that includes nonlinear forward propagation and scattering phenomena as [4,18]

$$\underbrace{\nabla^2 p(\underline{r}, t) - \frac{1}{c_0^2(\underline{r})} \frac{\partial^2 p(\underline{r}, t)}{\partial t^2}}_{(1) Linear\ propagation} + \quad (7)$$

$$\underbrace{\frac{\beta_{pa}(\underline{r})}{c_0^2(\underline{r})} \frac{\partial^2 p(\underline{r}, t)^2}{\partial t^2}}_{(2) Nonlinear\ propagation} \underbrace{- h_{ab}(\underline{r}, t) \otimes_t \frac{1}{c_0^2(\underline{r})} \frac{\partial^2 p(\underline{r}, t)}{\partial t^2}}_{(3) Absorption} =$$

$$\underbrace{\frac{\beta(\underline{r})}{c_0^2(\underline{r})} \frac{\partial^2 p(\underline{r}, t)}{\partial t^2} + \nabla(\gamma(\underline{r}) \nabla p(\underline{r}, t))}_{(4) Linear\ scattering\ source\ terms} - \underbrace{\frac{\sigma_n(\underline{r})}{c_0^2(\underline{r})} \frac{\partial^2 p(\underline{r}, t)^2}{\partial t^2}}_{(5) Nonlinear\ scattering\ source\ term}$$

$$c_0(\underline{r}) = \frac{1}{\sqrt{\rho_a(\underline{r}) \kappa_a(\underline{r})}}$$

$$\beta(\underline{r}) = \frac{\kappa_f(\underline{r})}{\kappa_a(\underline{r})}$$

$$\gamma(\underline{r}) = \frac{\rho_f(\underline{r})}{\rho_0(\underline{r})}$$

$$\sigma_n(\underline{r}) = \beta_{pf}(\underline{r}) + \beta_{pa}(\underline{r}) \beta(\underline{r})$$

where we have neglected $\nabla(1/\rho_a)$, the low amplitude terms $\beta\beta_{pf}$ of $\sigma_n$, and the $2^{nd}$ order $p^2$ term in the absorption. $c_0(\underline{r})$ is the linear wave propagation velocity for low field amplitudes. The left side terms determine the spatial propagation of the wave from the slowly varying components of the material parameters $c_0(\underline{r})$, $\beta_{pa}(\underline{r})$, and $h_{ab}(\underline{r}, t)$. The right side terms represent scattering sources that originate from the rapid spatial variation of the material parameters, $\beta(\underline{r})$, $\gamma(\underline{r})$, and $\sigma_n(\underline{r})$. $\beta(\underline{r})$ represents the rapid, relative variation of the isentropic compressibility, $\gamma(\underline{r})$ represents the rapid, relative variation of the mass density, while $\sigma_n(\underline{r})$ represents the rapid, relative variation of the nonlinear parameters $\beta_p(\underline{r})\kappa(\underline{r})$ of Eqs.(4,6) [4,18].

The linear propagation terms (1) of Eq.(7) guide the linear forward spatial propagation of the incident wave with propagation velocity $c_0(\underline{r})$ and absorption given by term (3), without addition of new frequency components. The linear scattering source terms (4) produce local linear scattering of the incident wave that has the same frequency components as the incident wave, with an amplitude modification of the components $\sim -\omega^2/c_0^2$ produced by the $2^{nd}$ order differentiation in the scattering terms, where $\omega$ is the angular frequency of the incident wave.

The slow variation of the nonlinear parameters give a value to $\beta_{pa}(\underline{r})$ that provides a nonlinear forward propagation distortion of the incident wave that accumulates in magnitude with propagation distance through term (2) of Eq.(7). A rapid variation of the nonlinear material parameters gives a value to $\sigma_n(\underline{r})$ that produces a local nonlinear distorted scattering of the incident wave through term (5) of Eq.(7).

Similar equations for elastic shear waves and electromagnetic waves can be formulated that represents similar propagation and local scattering phenomena, linear and nonlinear, for the shear and EM waves.

B. Nonlinear Propagation and Scattering for Dual Band Pulse Complexes

For estimation of non-linear material parameters, we transmit dual frequency pulse complexes where two examples are shown in FIG. 1. FIG. 1a shows a high frequency (HF) transmit pulse 101 propagating at the crest of a low frequency (LF) pulse 102, where FIG. 1b shows the same transmitted HF pulse 101 propagating at the through of the LF pulse 103, where the example is obtained by inversing the polarity of 102. For estimation of nonlinear parameters, we typically transmit at least two pulse complexes for each transmit beam direction, where the LF pulse varies in amplitude and/or polarity between at least two transmitted pulse complexes, where the LF pulse can be zero (i.e. no transmitted LF pulse) for a pulse complex, and the LF pulse is non-zero for at least one pulse complex. The HF:LF ratio is typically >5:1. For estimation of linear parameters we would preferably transmit only a HF pulse, i.e. the LF pulse is zero, or one could use the sum of the received HF signal from a positive and a negative LF pulse.

We study the situation where the total incident wave is the sum of the LF and HF pulses, i.e. $p(\underline{r},t) = p_L(\underline{r}, t) + p_H(\underline{r}, t)$. The nonlinear propagation and scattering are in this $2^{nd}$ order approximation both given by $$p(\underline{r}, t)^2 = (p_L(\underline{r}, t) + p_H(\underline{r}, t))^2 = \underbrace{p_L(\underline{r}, t)^2}_{nonlin\ self\ distortion} + \underbrace{2 p_L(\underline{r}, t) p_H(\underline{r}, t)}_{nonlin\ interaction} + \underbrace{p_H(\underline{r}, t)^2}_{nonlin\ self\ distortion} \quad (8)$$

Inserting Eq.(8) into Eq.(7) we can separate Eq.(7) into one equation for the LF and a second equation for the HF pulses as $$a) \underbrace{\nabla^2 p_L - \frac{1}{c_0^2} \frac{\partial^2 p_L}{\partial t^2}}_{(1) Linear\ propagation} + \underbrace{\frac{\beta_{pa}}{c_0^2} \frac{\partial^2 p_L^2}{\partial t^2}}_{(2b) Nonl\ prop\ self distortion} \underbrace{- h_{ab} \otimes_t \frac{\partial^2 p_L}{\partial t^2}}_{(3) Lin\ absorpt} = \quad (9)$$

$$\underbrace{\frac{\beta}{c_0^2} \frac{\partial^2 p_L^2}{\partial t^2} + \nabla(\gamma \cdot \nabla p_L)}_{(4) Linear\ scattering} - \underbrace{\frac{\sigma_n}{c_0^2} \frac{\partial^2 p_L^2}{\partial t^2}}_{(5b) Nonl\ selfd\ scatter\ source}$$

-continued $$b) \nabla^2 p_H - \underbrace{\frac{1}{c_0^2}\frac{\partial^2 p_H}{\partial t^2}}_{(1)\text{Linear propagation}} + \underbrace{\frac{2\beta_{pa}p_L}{c_0^2}\frac{\partial^2 p_H}{\partial t^2}}_{(2a)\text{Nonl interaction propag distortion}} + \underbrace{\frac{\beta}{c_0^2}\frac{\partial^2 p_H^2}{\partial t^2}}_{(2a)\text{Nonl prop selfdistortion}} - \underbrace{h_{ab} \otimes_t \frac{1}{c_0^2}\frac{\partial^2 p_H}{\partial t^2}}_{(3)\text{Absorption}} =$$

$$\underbrace{\frac{\beta}{c_0^2}\frac{\partial^2 p_H}{\partial t^2} + \nabla(\gamma(\underline{r})\nabla p_H)}_{(4)\text{Linear scattering source terms}} - \underbrace{\frac{2\sigma_n p_L}{c_0^2}\frac{\partial^2 p_H}{\partial t^2}}_{(5b)\text{Nonl interact source term}} - \underbrace{\frac{\sigma_n(\underline{r})}{c_0^2(\underline{r})}\frac{\partial^2 p_H^2}{\partial t^2}}_{(5b)\text{Nonl selfdist source term}}$$

where the material parameters $c_0(\underline{r})$, $\beta_{pa}(\underline{r})$, $\beta(\underline{r})$, $\gamma(\underline{r})$, $\sigma_n(\underline{r})$ all have spatial variation, and the wave fields and absorption kernel $p_L(\underline{r},t)$, $p_H(\underline{r},t)$, $h_{ab}(\underline{r},t)$ depend on space and time. We note that with zero LF pulse, the HF pulse propagates according to Eq.(9 b) with term (2b) and (5b) as zero. The low amplitude, linear propagation velocity is $c_0$ ($\underline{r}$) of Eq.(9) that produces linear propagation, term (1), modified by a self-distortion propagation term (2b), that is responsible for the harmonic propagation distortion utilized in harmonic imaging. The scattering is dominated by the linear term (4) where the self-distortion scattering term (5b) is important for scattering from micro-bubbles in a more complex form.

As shown in FIG. 1 we use a temporal HF pulse length $T_{pH}$ that is much shorter than half the period of the LF pulse, $T_L/2$, i.e. the bandwidth of the HF pulse $B_H > \omega_L/2$, where $\omega_L = 2\pi/T_L$ is the center angular frequency of the LF wave. For the further analysis we assume that $|2\beta_p(\underline{r})p_L(\underline{r},t)| = |x| << 1$ which allows the approximation $1-x \approx 1/(1+x)$. The propagation terms (1) and (2a) of the left side of Eq.(9b) can for the manipulation of the HF pulse by the co-propagating LF pulse be approximated as $$\underbrace{\nabla^2 p_H(\underline{r},t) - \frac{1}{c_0^2(\underline{r})}\frac{\partial^2 p_H(\underline{r},t)}{\partial t^2}}_{(1)\text{Linear propagation}} + \underbrace{\frac{2\beta_{pa}(\underline{r})p_L(\underline{r},t)}{c_0^2(\underline{r})}\frac{\partial^2 p_H(\underline{r},t)}{\partial t^2}}_{(2b)\text{Nonlinear interaction propagation}} \approx \quad (10)$$

$$\nabla^2 p_H(\underline{r},t) - \frac{1}{c_0^2(\underline{r})(1+2\beta_{pa}(\underline{r})p_L(\underline{r},t))}\frac{\partial^2 p_H(\underline{r},t)}{\partial t^2}$$

The numerator in front of the temporal derivative in this propagation operator is the square propagation velocity, and we hence see that the LF pulse pressure $p_L$ modifies the propagation velocity for the co-propagating HF pulse $p_H$ as $$c_0(\underline{r},p_L) = c_0^2(\underline{r})(1+2\beta_{pa}(\underline{r})p_L(\underline{r},t)) \approx c_0(\underline{r})\beta_{pa}(\underline{r})p_L(\underline{r},t) \quad (11)$$

where $p_L(\underline{r},t)$ is the actual LF field variable along the co-propagating HF pulse. Solving Eqs.(9a,b) for LF and HF transmit apertures with transmit pulse complexes as shown in FIG. 1, gives co-propagating LF and HF pulses along beams, where schematic examples of transmitted HF beams according to the invention are shown as beams 202, 605, 704, and 717 in FIG. 2, 6, 7. As the HF:LF ratio is typically >5:1, often ~20:1, the LF wavelength is >5-20 times the HF wave length. To minimize diffraction and keep the LF beam adequately collimated, the transmit aperture and beam for the LF pulse is typically much wider than for the HF pulse.

The HF pulse propagates close to the crest or trough of the LF pulses. The orthogonal trajectories of the HF pulse wave-fronts are paths of energy flow in the HF pulse propagation. We define the curves $\Gamma(\underline{r})$ as the orthogonal trajectories of the HF pulse wave-fronts that ends at $\underline{r}$. Let $p_c$ (s)=p·$p_{Lc}$(s) and $c_0$(s) be the LF pressure and linear propagation velocity at the center of gravity of the HF pulse at the distance coordinate s along $\Gamma(\underline{r})$, and p is a scaling factor for polarity and amplitude of the LF pulse. The propagation time-lag of the HF pulse at depth $\underline{r}$ along the orthogonal trajectories to the HF pulse wave-fronts, can then be approximated as $$t(\underline{r}) = \int_{\Gamma(\underline{r})} \frac{ds}{c(s,p_c(s))} \approx \int_{\Gamma(\underline{r})} \frac{ds}{c_0(s)} - \int_{\Gamma(\underline{r})} \frac{ds}{c_0(s)}\beta_{pa}(s)p_c(s) = t_0(\underline{r}) + \tau_p(\underline{r}) \quad (12)$$

$$t_0(\underline{r}) = \int_{\Gamma(\underline{r})} \frac{ds}{c_0(s)}$$

$$\tau_p(\underline{r}) = -p\int_{\Gamma(\underline{r})} \frac{ds}{c_0(s)}\beta_{pa}(s)p_{Lc}(s)$$

The propagation lag with zero LF pulse is $t_0(\underline{r})$ given by the propagation velocity $c_0(\underline{r})$ that is found with no LF manipulation of the tissue bulk elasticity. $\tau_\square(\underline{r})$ is the added nonlinear propagation delay (NPD) of the center of gravity of the HF pulse, produced by the nonlinear manipulation of the propagation velocity for the HF pulse by the LF pressure $p_c$(s) at the center of gravity of the HF pulse.

Variations of the LF pressure along the co-propagating HF pulse, outside the center of gravity of the HF pulse, produces a variation of the propagation velocity along the HF pulse, that in addition to the NPD produces a nonlinear pulse form distortion (PFD) of the HF pulse that accumulates with propagation distance. For HF pulses much shorter than the LF half period, as shown in FIG. 1, the PFD can be described by a filter. Defining $P_{tp}(\underline{r}, \omega)$ as the temporal Fourier transform of the transmitted HF pulse field that co-propagates with a LF pulse, and $P_{t0}(\underline{r}, \omega)$ as the HF pulse for zero LF pulse, the PFD filter is defined as $$P_{tp}(\underline{r}, \omega) = V_p(\underline{r}, \omega)P_{t0}(\underline{r}, \omega) \quad (13)$$

$$V_p(\underline{r}, \omega) = \frac{P_{tp}(\underline{r}, \omega)}{P_{t0}(\underline{r}, \omega)} = \tilde{V}_p(\underline{r}, \omega)e^{-i\omega\tau_p(\underline{r})}$$

and the subscript p designates the amplitude/polarity/phase of the LF pulse. $P_{tp}(\underline{r}, \omega)$ is obtained from the temporal Fourier transform of $p_H$ in Eq.(9b). $V_p$ includes all nonlinear forward propagation distortion, where the linear phase component of $V_p$ is separated out as the nonlinear propagation delay (NPD) $\sigma_p(\underline{r})$ up to the point $\underline{r}$ as described in Eq.(12). The filter $\tilde{V}_p$ hence represents the nonlinear pulse form distortion (PFD) of the HF pulse by the co-propagating LF pulse, and also the nonlinear attenuation produced by the nonlinear self-distortion of the HF pulse.

We note that when the 1$^{st}$ scattering/reflection occurs, the scattered LF pressure amplitude drops so much that after the scattering the LF modification of the propagation velocity is negligible for the scattered HF wave. This means that we only get essential contribution of the LF pulse to the NPD, $\tau_p(\underline{r})$ of Eq.(12), and the PFD, $\tilde{V}_p$, of Eq.(13), up to the 1$^{st}$ scattering, an effect that we will use to estimate the spatial variation of the nonlinear propagation parameter $\beta_{pa}(\underline{r})$, and the nonlinear scattering given by $\sigma_n(\underline{r})$, and suppress multiple scattered waves (noise) in the received signal to enhance the 1$^{st}$ order linear and nonlinear scattering parameters.

In summary, the nonlinear terms (2a, b) in Eq.(9b) produces a propagation distortion of the HF pulse as:
i) (2a): A nonlinear propagation delay (NPD) $\tau_p(\underline{r})$ produced by the LF pressure at the center of gravity of the co-propagating HF pulse according to Eq.(12), and is affected by the LF pulse up to the $1^{st}$ scattering, where the amplitude of the LF pulse drops so much that the nonlinear effect of the scattered LF pulse is negligible for the scattered HF wave.

ii) (2a): A nonlinear propagation pulse form distortion (PFD) of the HF pulse produced by the variation of the LF pulse field along the co-propagating HF pulse according to Eq.(13), and is affected by the LF pulse up to the $1^{st}$ scattering, where the amplitude of the LF pulse drops so much that the nonlinear effect of the scattered LF pulse is negligible for the scattered HF wave.

iii) (2b): A nonlinear self-distortion of the HF pulse which up to the $1^{st}$ scattering transfers energy from the fundamental HF band to harmonic and sub-harmonic components of the fundamental HF band, and is hence also found as a nonlinear attenuation of the fundamental band of the HF pulse. It is negligible after the $1^{st}$ scattering where the amplitude of the scattered HF pulse heavily drops.

The HF scattering cross section given in the right side of Eq.(9b) is composed of a linear component. term (4), and a nonlinear component, term (5), where term (5a) takes care of the variation of the HF fundamental band scattering produced by the LF pulse, while term (5b) represents self distortion scattering that produces scattered signal in the harmonic and sub-harmonic components of the HF-band. This scattering term is however so low that it can be neglected, except for micro-bubbles at adequately low frequency, where the scattering process is described by a differential equation, i.e. highly frequency dependent scattering with a resonance frequency, producing a well known, more complex Rayleigh-Plesset term for HF self distortion scattering.

Because the temporal pulse length of the HF pulse $T_{pH} \ll T_L/2$, we can approximate $p_L(\underline{r}) \approx p_c(\underline{r})$ also in the interaction scattering term (5a) of Eq.(9 b)

$$\underbrace{\frac{2\sigma_n p_L}{c_0^2} \frac{\partial^2 p_H}{\partial t^2}}_{(5b) \text{Interaction scatt}} \approx \underbrace{\frac{2\sigma_n(\underline{r})p_c(\underline{r})}{c_0^2(\underline{r})} \frac{\partial^2 p_H(\underline{r}, t)}{\partial t^2}}_{(5b)LF-HF \text{ Interaction scattering}} \quad (14)$$

where $p_c(\underline{r})$ is the LF pressure at the center of gravity of the co-propagating HF pulse as for the NPD propagation term in Eq.(12).

The scattering from the rapid, relative fluctuations in the compressibility, $\beta(\underline{r})$, is a monopole term that from small scatterers (dim<~¼ HF wave length) give the same scattering in all directions, while the scattering from the rapid, relative fluctuations in the mass density, $\gamma(\underline{r})$, is a dipole term where the scattering from small scatterers depends on cosine to the cross-angle between the transmit and receive beams [18]. For a given cross-angle between the transmit and receive beams one can hence for the fundamental HF band write the scattering coefficient as a sum of a linear scattering coefficient and a nonlinear scattering coefficient as $$\sigma(\omega, \underline{r}, p_c) = -\frac{\omega^2}{c_0^2}[\sigma_l(\underline{r}) + 2p_c(\underline{r})\sigma_n(\underline{r})] \quad (15)$$

$\sigma_l(\underline{r})$ represents the sum of the linear scattering from fluctuations in compressibility and mass density. For larger structures of scatterers (dim>~HF wave length), like for example layers of fat, muscle, connective tissue, or a vessel wall, the total scattered wave will be the sum of contributions from local parts of the structures which gives a directional scattering also influenced by the detailed shape of the structures [18].

The effect of the low frequency (LF) pulse on the received HF signal, can hence be split into three groups with reference to Eq.(9 b):

Group A is the effect of the nonlinear propagation term (2a). It is found in the received signal with transmission through the object with tomographic measurements, and in the linearly scattered signal from term (4). It represents the accumulative nonlinear propagation distortion of the HF incident pulse produced by the LF pulse, i.e. term (2a). This group is split into a nonlinear propagation delay (NPD) according to Eq.(12) (i above), and nonlinear pulse form distortion (PFD) according to Eq.(13) (ii above), and Group B originates directly in the local nonlinear interaction scattering of the LF on the HF pulse, i.e. term (5a), where the local LF pulse pressure at the co-propagating HF pulse exerts an amplitude modulation of the scattered wave, proportional to $p_c(\underline{r})$. It is generally useful for detection of micro-bubbles and micro-calcifications, and Group C. This is found as local nonlinear self distortion scattering from term (5b) of the forward accumulative nonlinear propagation components in the incident wave. However, typical nonlinear material parameters are so low that this group is negligible, except for micro-bubbles and micro-calcifications in some situations.

5.2 Methods and Instruments for Measurement and Estimation

Example embodiments of the invention will now be described in relation to the drawings. The methods and structure of the instrumentation are applicable to both electromagnetic (EM) and elastic (EL) waves, and to a wide range of frequencies with a wide range of applications. For EL waves one can apply the methods and instrumentation to both shear waves and compression waves, both in the subsonic, sonic, and ultrasonic frequency ranges. We do in the embodiments describe by example ultrasonic measurements or imaging, both for technical and medical applications. This presentation is meant for illustration purposes only, and by no means represents limitations of the invention, which in its broadest aspect is defined by the claims appended hereto.

Figure 2:
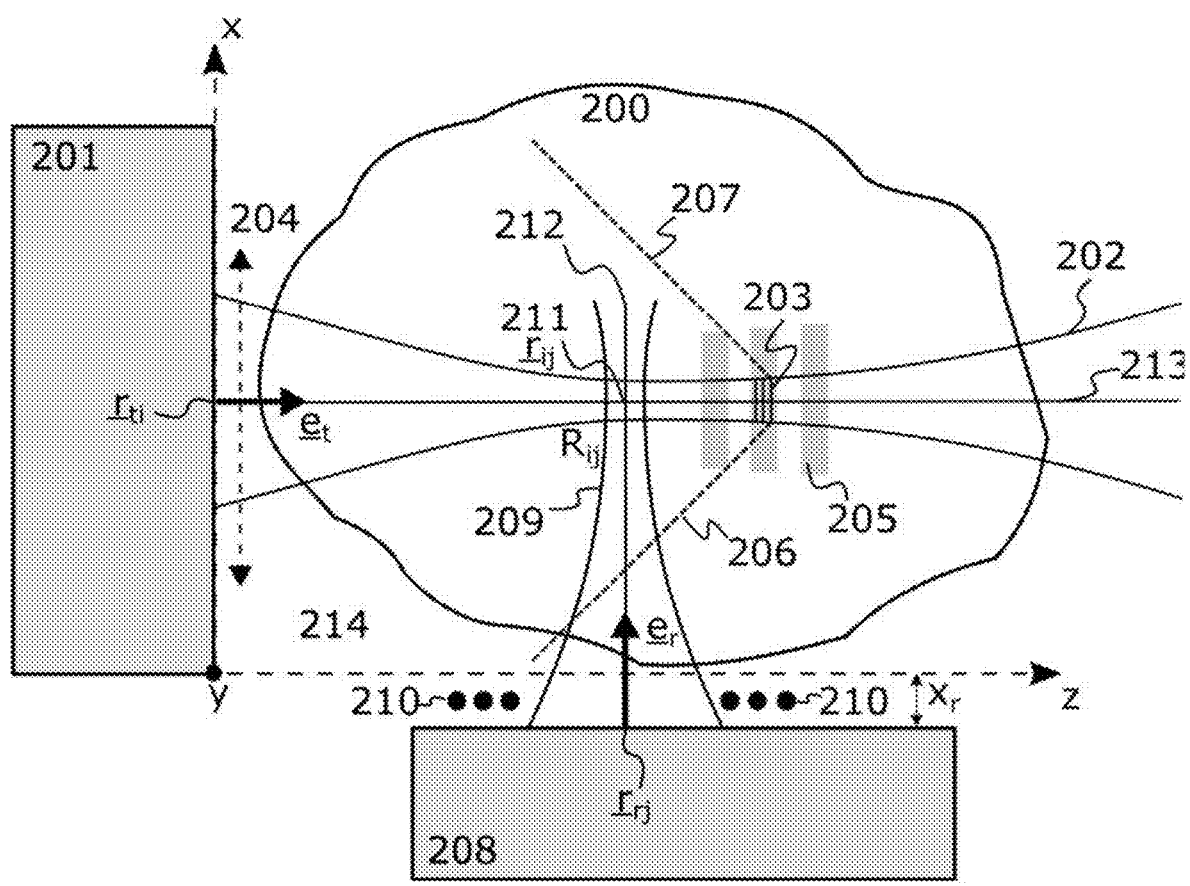
FIG. 2 shows a measurement setup to obtain acoustic measurements for estimation of HF received signals for one or both of estimation and imaging of several image signals related to the nonlinear material parameters of the material.

FIG. 2 shows by example an instrument setup according to the invention for measurement and estimation of local linear, and nonlinear propagation and scattering parameters in the object 200. 201 shows a transmit array system for transmission of pulses into the object. Acoustic contact between the transmit and receive (208) arrays can for example be obtained by immersing the object in a fluid (214), e.g. water, which for example is common with breast tomography, (FIG. 6), or other types of acoustic stand-off between the receive probe and the object, or direct contact between the probes and the object. With EM waves vacuum forms a good contact between the transmitters and the object, while fluids or soft tissue can provide contact for adequately small dimensions.

For estimation of nonlinear parameters the methods comprises transmitting at least two pulse complexes composed of co-propagating high frequency (HF) and low frequency (LF) pulses, where said HF pulse propagates close to the crest or trough of the LF pulse along at least one HF transmit beam, and where at least one of the amplitude and polarity of the LF pulse varies between at least two transmitted pulse complexes, where the amplitude of the LF pulse can be zero for a pulse complex and the amplitude of at least one LF pulse of said at least two transmitted pulse complexes is non-zero, as described in relation to FIG. 1 above. A preferred embodiment would be arranged to estimate both linear and nonlinear parameters, where 201 would be arranged to be able to transmit dual band pulse complexes, also including a zero LF pulse.

An example HF beam in the object is indicated as 202, with the HF pulse propagating to the right along the beam indicated as 203 at a particular time in the propagation. A LF pulse is, at the same time point, indicated as 205 with the positive swings as grey, co-propagating with the HF pulse to the right to manipulate both the propagation velocity and the scattering of the HF pulse, as discussed in Section 5.1B above. The HF pulse is indicated to be located at the crest of the LF pulse as indicated in FIG. 1a. The HF pulse is scattered both linearly and nonlinearly, Eqs.(9b, 14, 15) as it propagates along the beam, and generates a scattered HF wave field propagating as a Mach-cone indicated by the front waves 206 and 207.

208 shows a HF receive array and processing system, where the Figure shows by example one HF receive cross-beam 209, where the HF receive cross-beam axis 212 crosses the HF transmit beam axis 213 at 211. An x-y-z Cartesian coordinate system shows the HF transmit beam axis along the z-direction and the HF receive cross-beam in the x-direction, where the x-axis is in the paper plane, and the y-axis is vertical to the paper plane. In this example, the coordinate system is defined so that the HF transmit aperture has the center $\underline{r}_{ti}=(x_i, y_i, 0)$, and the HF receive cross-beam aperture has the center at $\underline{r}_{rj}=(-x_i, y_j, z_j)$, preferably with focus at the crossing of the HF transmit and receive beam axes. The overlap of the HF transmit and receive beams define a cross-beam observation cell $R_{ij}$ of scatterers, centered at 211 with the position $\underline{r}_{ij}=(x_i,y_i,z_j)$ that defines an image measurement point $\underline{r}$.

With single HF transmit and receive cross-beams one will observe a scattered signal from a single cross-beam observation cell $R(\underline{r})$ centered at $\underline{r}$. However, scanning the HF receive cross-beam axis along the HF transmit beam axis as indicated by the dots 210, allows measurement of scattered HF cross-beam receive signals from cross-beam observation cells centered at a set of crossing positions $\underline{r}_{ij}$ between the HF transmit axis starting at $\underline{r}_{ti}$, and receive beam axes starting at $\underline{r}_{rj}$, j=1, . . . , J. This can be done in time series by transmitting a LF-HF pulse complex for each HF receive cross-beam position, or with time parallel HF receive beam forming with focus at several locations along the HF transmit beam, for measurements of the scattered HF cross-beam receive signal at these locations along the HF transmit beam. The array 208 can for example be a linear array, or a phased array, receiving in parallel on all elements where the element signals are coupled to a parallel receive beam former, producing in parallel individual receive signals for a set of receive cross-beams, all focused at different locations on the HF transmit beam axis.

For 2D or 3D imaging, one can use as system set up to scan the LF-HF transmit beam laterally (x-direction) or vertically (y-direction) as indicated by the arrows 204, in order to irradiate a 2D or 3D section of at least a region of the object. With a matched scanning of the HF receive cross-beam focus along each HF transmit beam axes, gives a 2D/3D set of HF cross-beam receive signals scattered from cross-beam observation cells $R_{ij}$ defined by the crossings of the HF transmit and receive beams and centered at the crossing of the HF transmit and receive cross-beam axes at $\underline{r}_{ij}$. We label the positions of the array origin of the HF transmit beam axes by the coordinate vectors $\underline{r}_{ti}$, i=1, . . . , I, and the positions of the array origin of the receive beam axes by the coordinate vectors $\underline{r}_{rj}$, j=1, . . . , J. The distance between transmit beam axes is $\Delta r_t$, and between the receive beam axes the distance is $\Delta r_r$. Note that to minimize the dimension of $R_{ij}$ one would adjust the aperture and focus of the HF receive cross-beams for narrow receive focus at the actual HF transmit beam axis.

The HF cross-beam receive signals are processed in the receive unit 208 to provide linear and nonlinear propagation and scattering parameters for each measurement point $\underline{r}_{ij}$, in the scanned region with spatial resolution given by the dimension of the cross-beam observation cells $R_{ij}$, as described below. The unit 208 also contains a display system for the images. To give an impression of a continuous image in the display, one typically introduces interpolated image display values between the image measurement points $\underline{r}_{ij}$.

To simplify notation in the equations below, we label $\underline{r}_{ij}=\underline{r}$. The HF cross-beam receive signals are composed of three components: i) a linear scattering component $y_{lp}(t,\underline{r})$, and ii) a nonlinear scattering component $2p_C(\underline{r})y_{np}(t,\underline{r})$ where $p_c$ is the LF pulse amplitude defined in Eq.(12,14), and iii) followed by a multiple scattering component $n_p(t,\underline{r})$, illustrated in FIG. 3. The receive signal for each measurement point $\underline{r}$ can hence be modeled as $$y_p(t,\underline{r})=y_{lp}(t,\underline{r})+2p_c(\underline{r})y_{np}(t,\underline{r})+n_p(t,\underline{r})$$

$$y_{l/np}(t,\underline{r})=\int d^3r_0 A(\underline{r}-\underline{r}_0,\underline{r})u_p(t-\tau_p(\underline{r})-\tau_f(\underline{r}-\underline{r}_0,\underline{r})-(|\underline{r}_0-\underline{r}_t|+|\underline{r}_0-\underline{r}_r|)/c_0,\underline{r})\sigma_{l/n}(\underline{r}_0) \quad (16)$$

where we have defined p as a scaling and polarity factor of the LF pressure as in Eq.(12), i.e. $p_c(\underline{r})=p\cdot p_{LC}(\underline{r})\cdot \underline{r}_0=(x_0, y_0, z_0)$ is the scatterer source point, and $\sigma_l(\underline{r}_0)$ and $\sigma_n(\underline{r}_0)$ are the linear and nonlinear HF scattering densities from Eqs.(9b, 14,15). The combined HF receive, $A_r$, and HF transmit beam, $A_t$, amplitude weighting around the image measurement point $\underline{r}=(x, y, z)$ defines the cross-beam observation cells $A(\underline{r}-\underline{r}_0,\underline{r})=A_r(y-y_0,z-z_0,x)A_t(x-x_0,y-y_0,z)\cdot u_p(\cdot,\underline{r})$ is the received HF pulse from a point scatterer within the cross-beam observation cell $\underline{R}(\underline{r})$ centered around the image point $\underline{r}$, that observes a nonlinear propagation delay (NPD) $\tau_p(\underline{r})$ according to Eq.(12), a nonlinear pulse form distortion (PFD) according to Eq.(13), and a propagation nonlinear self distortion according to Eq.(9 b, term 2b) for the HF transmit pulse propagation up to depth $\underline{r}$. The NPD and PFD vary so slowly with position that we approximate it as constant within each observation cell.

$\tau_f(\underline{r}-\underline{r}_0,\underline{r})=\tau_t(\underline{r}-\underline{r}_0,z)+\tau_r(\underline{r}-\underline{r}_0,x)$ is the sum of the HF transmit beam focusing phase delay $\tau_t$ and the HF receive beam focusing phase delay $\tau_r$, and $|\underline{r}_0-\underline{r}_t|+|\underline{r}_0-\underline{r}_r|$ is the total propagation distance of the pulse from the transmit aperture centered at $\underline{r}_t$ to the scatterer at $\underline{r}_0$ and to the receiver aperture centered at $\underline{r}_r$. Close to the focus of a HF receive or transmit beam we can approximate $\tau_r$ or $\tau_t \approx 0$. A preferred system allows for adjustment of the HF receive cross-beam focus onto the HF transmit beam axis, which allows the approximation $\tau_r \approx 0$ in the observation cell, while for a fixed transmit focus $\tau_t \approx 0$ for $\underline{r}$ outside the HF transmit focus.

Lateral filtering of the HF cross-beam receive signal provides a synthetic focusing in the actual image range, as discussed in relation to Eqs.(18,19) below. This allows the approximation of both $\tau_t, \tau_r \approx 0$.

Schematic example received scattered signals from example HF receive cross-beam 209/210 are shown in FIG.

3 at a given image point $\underline{r}=(x,y,z)$. The upper signal 301 shows the situation when the HF pulse propagates close to the positive crest of the LF pulse as in FIG. 1a, the middle signal 302 shows the situation when the LF pulse is zero, and the lowest signal 303 shows the situation when the LF pulse is inverted so that the HF pulse propagates close to the trough of the LF pulse as in FIG. 1b. All signals comprises a first part 304 generated by $1^{st}$ order scattering from the cross-beam observation cell $R(\underline{r})$ around $\underline{r}=(x,y,z)$ with a propagation time lag given by the distance $|\underline{r}_0-\underline{r}_t|+|\underline{r}_0-\underline{r}_r|$ in the models of Eqs.(14-16). After this $1^{st}$ part of the scattered signal follows a tail of weaker signals 305 that is the multiple scattered signal $n_p(t,\underline{r})$ within the HF transmit beam before the last scattering in the overlap between the receive beam and the multiple scattered beam.

From Eqs.(11,12) we see that p>0 provides a nonlinear increase in the HF propagation velocity that advances the arrival time (negative delay) of the scattered signal compared to for p=0, and p<0 provides a nonlinear decrease in the HF propagation velocity that delays the arrival time (positive delay) of the scattered signal compared to that for p=0. The 304 part of 301 is an advancement of the 304 part of 302, i.e. a negative NPD $\tau_+(\underline{r})<0$ according to Eq.(12). The 304 part of 303 is in the same way a delay of 302, i.e. a positive NPD $\tau_-(\underline{r})>0$, where the subscript + and − and 0 indicates with reference to FIG. 1, measurements with a positive (102), negative (103) and zero transmitted LF pulse. The amplitude of the LF pulse drops so much in the $1^{st}$ scattering that the advancement/delay of the multiple scattered signal $n_p(t,\underline{r})$ (305) is much less than for the $1^{st}$ part 304. Crossing side lobes, grating lobes and edge waves of the transmit and receive beams can add noise components that arrives before the $1^{st}$ order scattered component 304 from the cross-beam observation cell. These noise components are suppressed by proper apodization of transmit and receive beam apertures. Temporal Fourier transform of the front part 304 of the received signal in Eq.(16) gives $$Y_p(\omega,\underline{r})=U_p(\omega,\underline{r})e^{-i\omega\tau_p(\underline{r})}[X_l(\omega,\underline{r})+2p_c(\underline{r})X_n(\omega,\underline{r})]$$

$$X_{l/n}(\omega,\underline{r})=\int d^3r_0 A(\underline{r}-\underline{r}_0,\underline{r})e^{-i\omega(\tau_f(\underline{r}-\underline{r}_0,\underline{r})+(|\underline{r}_0-\underline{r}_t|+|\underline{r}_0-\underline{r}_r|)/c_0)}\sigma_{l/n}(\underline{r}_0) \quad (17)$$

where $X_l(\omega,\underline{r})$ and $X_n(\omega,\underline{r})$ are the temporal Fourier transforms of the linear and nonlinear scattering components from the cross-beam observation cell centered at $\underline{r}$. The exponential function arises from the delay components in the temporal argument of up in Eq.(16).

The nonlinear self-distortion according to Eq.(9 b, term 2b) introduces harmonic components of the fundamental band of the HF transmit pulse that varies with depth in a balance between propagation distance and absorption of the transmitted HF pulse. Through well-known methods of radiofrequency filtering of the receive HF signal, or the use of pulse inversion where one transmits two pulse complexes with opposite polarity of the HF pulse and the same LF pulse, one can extract harmonic components of $Y_p(\omega, \underline{r})$ for further processing in the receive processor, as described in front of the FIG. 8 description below.

One will ideally set a narrow focus of the HF receive cross-beam essentially on the transmit beam axis. In the y- and z-directions the observation region is therefore generally limited by a narrow receive beam, but in the x-direction the observation region is limited by the x-width of the transmit beam. As the transmit beam operates with a fixed transmit focus, the transmit beam width varies with depth z outside the focus. For z outside the focal region, the HF transmit beam can therefore be wide both in the azimuth (x-) and elevation (y-) directions.

When 3D scanning of a stationary object is available, one can obtain synthetically focused transmit and receive beams through spatial filtering of measurement signals as $$\hat{Y}_p(\omega,\underline{r})=\int d^3r_0 W(\omega,\underline{r}-\underline{r}_0,\underline{r})Y_p(\omega,\underline{r}_0)$$

$$W(\omega,\underline{r}-\underline{r}_0,\underline{r})=B(\omega,\underline{r}-\underline{r}_0,\underline{r})e^{i\omega\tau_f(\underline{r}-\underline{r}_0,\underline{r})} \quad (18)$$

where B is a weighting function to reduce spatial side-lobes of the filter. The filter kernel can be obtained from simulation of the transmit and receive beams to obtain $\tau_t(\underline{r}-\underline{r}_0,\underline{r})$ and $\tau_r(\underline{r}-\underline{r}_0,\underline{r})$. Eqs.(31-33) below also present methods of estimating $\tau_t(\underline{r}-\underline{r}_0,\underline{r})$ and $\tau_r(\underline{r}-\underline{r}_0,\underline{r})$ that corrects for wave front aberrations due to spatial variations in the propagation velocity within the object. The filter amplitude weighting B, can conveniently be proportional to the amplitude of the simulated beams, potentially with added windowing. When the receive beam is focused onto the transmit beam axis, we can approximate $\tau_r \approx 0$ within the observation region. The integration is then done over the transversal coordinate to the transmit beam axis, $\underline{r}_\perp=(x,y)$, as $$\hat{Y}_p(\omega,\underline{r})=\int d^2r_\perp W(\omega,\underline{r}-\underline{r}_\perp,z)Y_p(\omega,\underline{r}_\perp,z)$$

$$W(\omega,\underline{r}-\underline{r}_\perp,z)=B(\omega,\underline{r}-\underline{r}_\perp,z)e^{i\omega\tau_t(\underline{r}-\underline{r}_\perp,z)} \quad (19)$$

When the y-width of the receive beam focus is sufficiently narrow, the integration over $\underline{r}_\perp$ can be approximated by an integration in the x-direction (azimuth) only, with a filter adapted for use with 2D scanning of the transmit beam in the x-direction.

One advantage of the synthetic focusing is that the cross beam observation cell is reduced, and the approximation that the NPD and PFD are constant in the observation cell becomes more accurate, i.e. improves the approximation of taking $\tau_p(\underline{r})$ and $U_p(\omega, \underline{r})$ outside the integral in Eqs.(17). The synthetic focus filtering also provides images with improved spatial resolution.

From the models in Eqs.(12, 16, 17), we can determine $\tau_p(\underline{r})$ from the delay between the front parts 304 of two of the signals 301-303, or all three signals in combination. This can for example be done through correlation between the $1^{st}$ order scattered front part 304 of the HF cross-beam receive signals from pulse complexes with different LF pulses, or by measuring the arrival time difference between the front edge or the maximum amplitude of the signals, or a combination of these. An advantage of the method as described is that we have first intervals of the measured signals that comprises mainly $1^{st}$ order scattering, which gives a clear definition of $\tau_p(\underline{r}_t,z)$ in Eq.(12) at depth z along the transmit beam axis starting at $\underline{r}_t$. A schematic example of $\tau_-(\underline{r}_t,z_j)$ is shown as 401 in FIG. 4.

Figure 4:
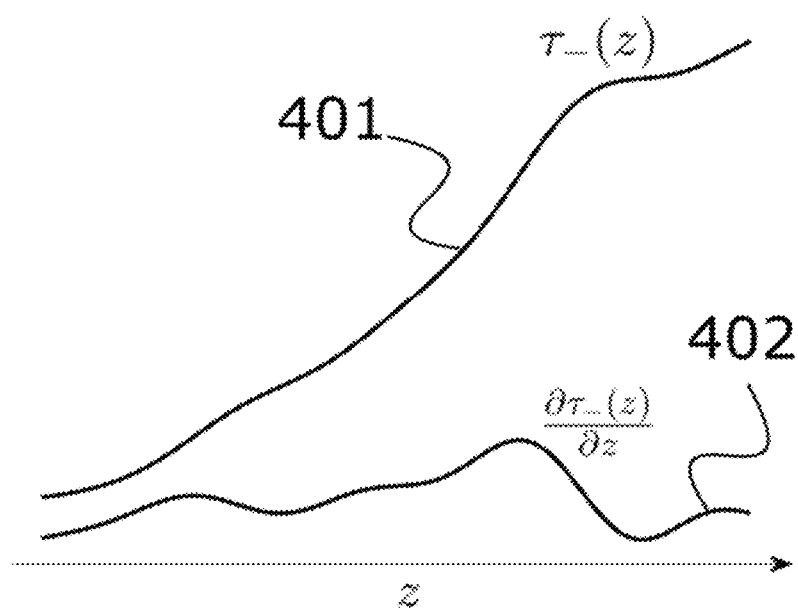
FIG. 4 shows examples of an estimated nonlinear propagation delay (NPD) and its gradient along the HF pulse propagation direction.

Having measured $\tau_p(\underline{r}_t,z_j)$ at a set of points $z_j$ with distance $\Delta z$ we can from Eq.(12) estimate the nonlinear propagation parameter $$\beta_{pa}(\underline{r}_t, z_j) \approx -\frac{c_0(\underline{r}_t, z_j)}{p_c(\underline{r}_t, z_j)} \frac{\tau_p(\underline{r}_t, z_j) - \tau_p(\underline{r}_t, z_{j-1})}{\Delta z} \quad (20)$$

where 402 in FIG. 4 shows by example the z-differential of $\tau_-$. From the description of Eq.(12), $p_c(\underline{r}_t,z_j)$ is the LF pressure approximately at the center of gravity of the HF pulse, and $c_0(\underline{r}_t,z_j)$ is the linear propagation velocity at the same position, i.e. $z_j$ along the transmit beam axis starting at $\underline{r}_t$. The spatial variation of $c_0(\underline{r}_t,z_j)$ in soft tissue is ~±4%, and is for image reconstruction approximated by a constant 1540 m/s, which is also a useful approximation in Eq.(20-22). As described in relation to Eqs.(29,30) below, one can obtain local estimates of $c_0(\underline{r})$ from a first estimate of $\beta_{pa}(\underline{r}_t,z)$ with constant $c_0$, and then modify the first estimate of $\beta_{pa}(\underline{r}_t,z)$ with the new estimate $c_0(\underline{r})$, for example in an iterative procedure. With a ring array as in FIG. 6 one can estimate locally varying $c_0(\underline{r})$ with tomographic methods [13-16], and use this estimate in Eqs.(20-22). This opens for a combination of $\beta_p$ and $c_0$ for the tissue characterization, as discussed below. Low-pass filtered differentiation can be obtained by combining more samples of the NPD at different depths along the HF transmit beam, for example as $$\beta_{pa}(\underline{r}_t, z_j) \approx -\frac{c_0(\underline{r}_t, z_j)}{p_c(\underline{r}_t, z_j)} \sum_{n \in N} a_n \tau_p(\underline{r}_t, z_n) \quad (21)$$

where an are filtering coefficients and N describes an interval of terms. Allowing for reduced spatial resolution in the estimate of $\beta_{pa}$, one can also in Eq.(21) include weighted sums along neighboring transmit beams (i.e. along $\underline{r}_t$) to reduce noise in the estimate, according to known methods. One can also use nonlinear differentiation, for example through minimizing a functional of the form $$J\{\beta_{pa}(\underline{r}_t, z)\} =$$

$$\int_I dz \left\{ W_\beta(\underline{r}_t, z) \left| \tau(\underline{r}_t, z) - \int_0^z \frac{dz_0}{c_0} \cdot \beta_{pa}(\underline{r}_t, z_0) p_{LF}(\underline{r}_t, z_0) \right| + \right.$$
$$\left. W_n(\underline{r}_t, z) |\beta_{pa}(\underline{r}_t, z)_z| \right\} \quad (22)$$

Subject to constraints: $\beta_{p,min} < \beta_{pa}(\underline{r}_t, z) < \beta_{p,max}$ where $\beta_{pa}(\underline{r}_t,z)_z$ denotes the gradient with respect to z, and $W_\beta$ and $W_n$ are weights to be chosen to balance between rapid response to spatial changes in $\beta_p()$ for high values of $W_\beta/W_n$, and noise reduction for low values of $W_\beta/W_n$. We can also include integration/summation for neighboring transmit beams, i.e. along $\underline{r}_t$ to reduce noise at the cost of lower spatial resolution, as for the linear estimation in Eq.(21).

Figure 5:
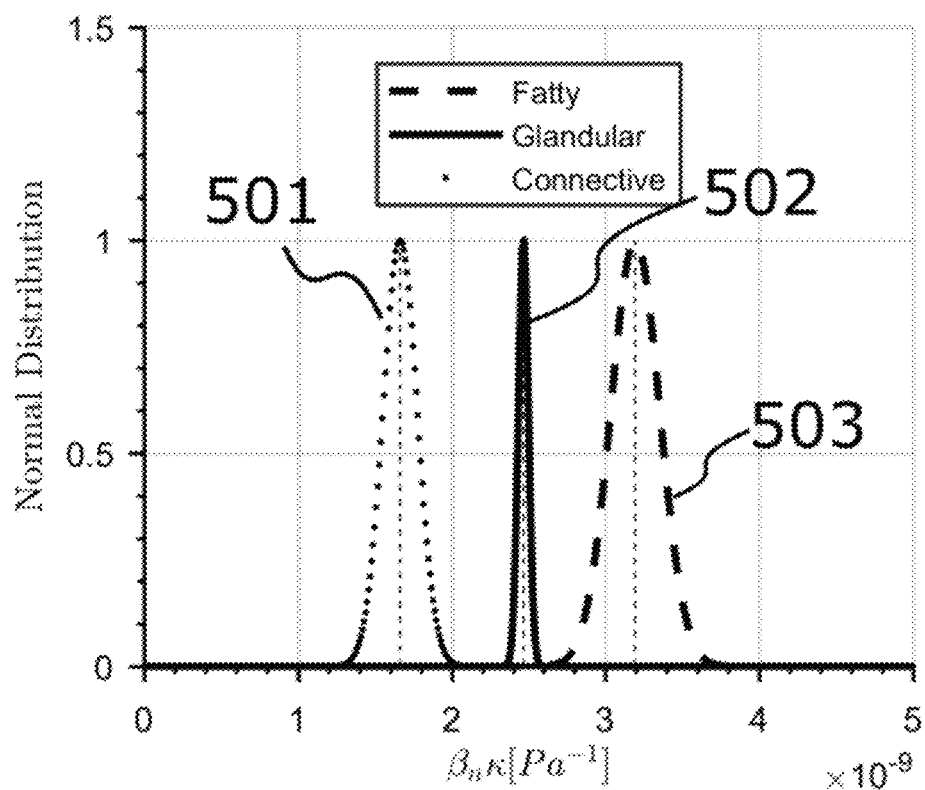
FIG. 5 shows variation of the nonlinear elasticity parameter $\beta_p = \beta_n \kappa$ for connective tissue, breast glandular tissue, and fat.

With a 2D or 3D scanning of the transmit and receive beams, we note that Eqs.(20-22) presents a quantitative spatial imaging of the nonlinear elastic tissue parameter, where FIG. 5 shows by example typical values of $\beta_{pa}=\beta_{na}\kappa_a$, for connective (501), glandular (502), and fat (503) tissues in breast from [10]. We note that the difference of $\beta_p$ between the different tissues is so large that it makes estimation of the $\beta_p$ parameter very interesting for tissue characterization, for example detection and characterization of cancer tumors and atherosclerotic arterial plaque.

The nonlinear scattering is found at highly local points from micro-bubbles and hard particles like micro-calcifications, and the nonlinear pulse form distortion (PFD) can hence from Eqs.(13, 17-19) be estimated as $$\tilde{V}_\pm(\omega, z, \underline{r}_t) = \frac{U_\pm(\omega, z, \underline{r}_t)}{U_0(\omega, z, \underline{r}_t)} = \frac{\hat{Y}_\pm(\omega, z, \underline{r}_t) e^{i\omega\tau_\pm(z,\underline{r}_t)}}{\hat{Y}_0(\omega, z, \underline{r}_t)} \quad (23)$$

We define a Wiener form of inversion of $\tilde{V}_p(z,\omega;\underline{r}_t)$ as $$H_{+/-}(\omega, z; \underline{r}_t) = \frac{1}{\tilde{V}_{+/-}(\omega, z; \underline{r}_t)} \frac{1}{1 + \mu/|\tilde{V}_{+/-}(\omega, z; \underline{r}_t)|^2} \quad (24)$$

where the parameter $\mu$ is adjusted to maximize the signal to noise ratio in the filtered signal.

$\hat{Y}_p(\omega,\underline{r}_i)$ as given in Eqs.(17-19) for image points $\underline{r}_{ij}$ is subject to absorption of the HF pulse both along the HF transmit and the HF receive cross-beams. When estimates of the tissue absorption exist, for example from ultrasound tomography imaging [13-17], the absorption can be compensated for. When such estimates do not exist, it is in ultrasound imaging common to use a depth varying gain control, either set manually or through some automatic estimation. Assuming that the receive signal in Eqs.(16-19) has undergone some depth gain adjustment to compensate for absorption, we can from Eqs.(17-19) obtain absorption compensated estimates of the linear and nonlinear scattering components as $$\hat{X}_l(\omega, \underline{r}_i) = \quad (25)$$
$$\frac{1}{2}\left(H_+(\omega, \underline{r}_i)e^{i\omega\tau_+(\underline{r}_i)}\hat{Y}_+(\omega, \underline{r}_i) + H_-(\omega, \underline{r}_i)e^{i\omega\tau_-(\underline{r}_i)}\hat{Y}_-(\omega, \underline{r}_i)\right)$$

$$\hat{X}_n(\omega, \underline{r}_i) =$$
$$\frac{1}{4|p_c(\underline{r}_i)|}\left(H_+(\omega, \underline{r}_i)e^{i\omega\tau_+(\underline{r}_i)}\hat{Y}_+(\omega, \underline{r}_i) - H_-(\omega, \underline{r}_i)e^{i\omega\tau_-(\underline{r}_i)}\hat{Y}_-(\omega, \underline{r}_i)\right)$$

We could then for example display $|\hat{X}_l(\omega,\underline{r}_i)|$ and $|\hat{X}_n(\omega,\underline{r}_i)|$ at a typical frequency, say the center frequency $\omega_0$ of the fundamental HF band or a harmonic of the fundamental HF band, or an average of $|\hat{X}_l|$ and $|\hat{X}_n|$ across a band B of strong frequency components within the HF fundamental or harmonic bands, for example $$D_l(\underline{r}_i) = \frac{1}{B}\int_B d\omega |\hat{X}_l(\omega, \underline{r}_i)| \quad (26)$$

$$D_n(\underline{r}_i) = \frac{1}{B}\int_B d\omega |\hat{X}_n(\omega, \underline{r}_i)|$$

Other alternatives are to show the average of the square $|\hat{X}_{l/n}(\omega,\underline{r}_i)|^2$.

When $p_c$ is unknown, we still get an interesting visualization of the spatial variation of the nonlinear scattering without the scaling of $1/p_c$ in Eqs.(14), similar to Eq.(20,21) for the nonlinear elasticity parameter, for example to detect and visualize micro-bubbles or micro-calcifications in the tissue. When estimates of local absorption are available, these can be combined with Eq.(25) by anyone skilled in the art to obtain quantitative estimates of both linear and nonlinear scattering, that is useful for tissue characterization, for example of cancer tumors and atherosclerotic plaques.

Figure 3:
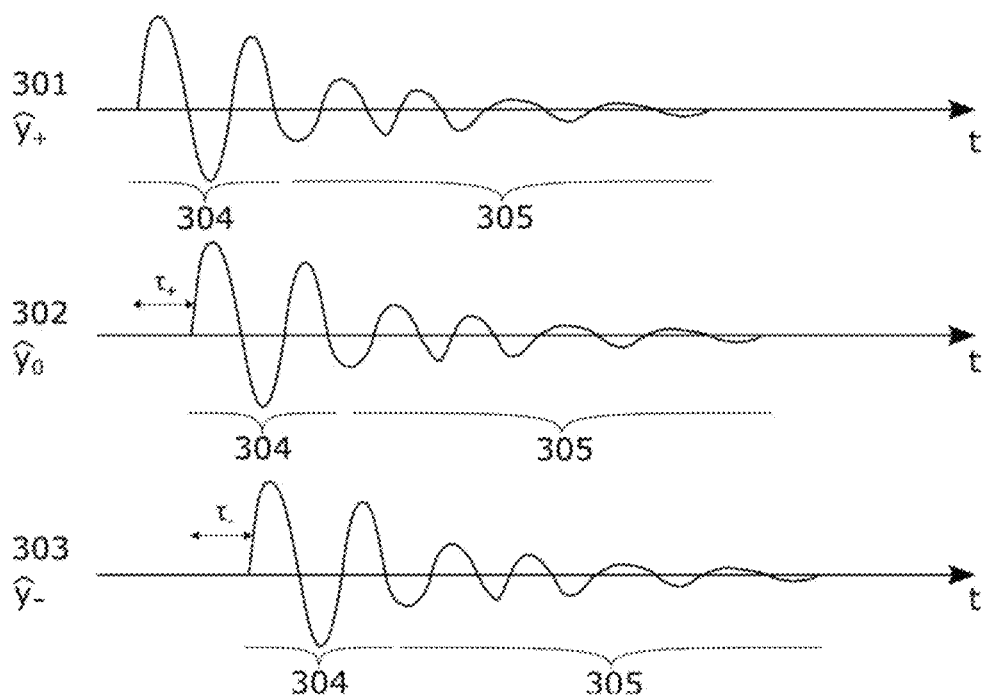
FIG. 3 shows by example typical HF receive signals for different transmitted LF pulses.

We notice from Eqs.(16-19) that several scatterers within the cross-beam observation cell can participate to the front signal 304 in FIG. 3, which produces an interference pattern (speckle) in this part of the signal that depends on the relative position between the participating scatterers and the directions of the HF transmit and receive cross-beams. Using several HF receive cross-beams crossing the HF transmit beam with different directions at the same image position $\underline{r}$, as shown by the examples 609, 612 in FIGS. 6 and 704, 705 in FIG. 7a, then provides several HF receive signals with different speckle (interference patterns) that can be used for statistical averaging in the signal processing to reduce random errors in the estimation of the nonlinear propagation and scattering parameters. In the example system shown in FIG. 2 we could for example within this frame of thinking also use HF receive cross-beams with different directions, and also have HF receive beams crossing the HF transmit beam in the opposite direction of 209 at the image point r at 211. This would require a HF receive array at the opposite side of the object that still could be operated by the same parallel HF receive beam former as 209.

Figure 6:
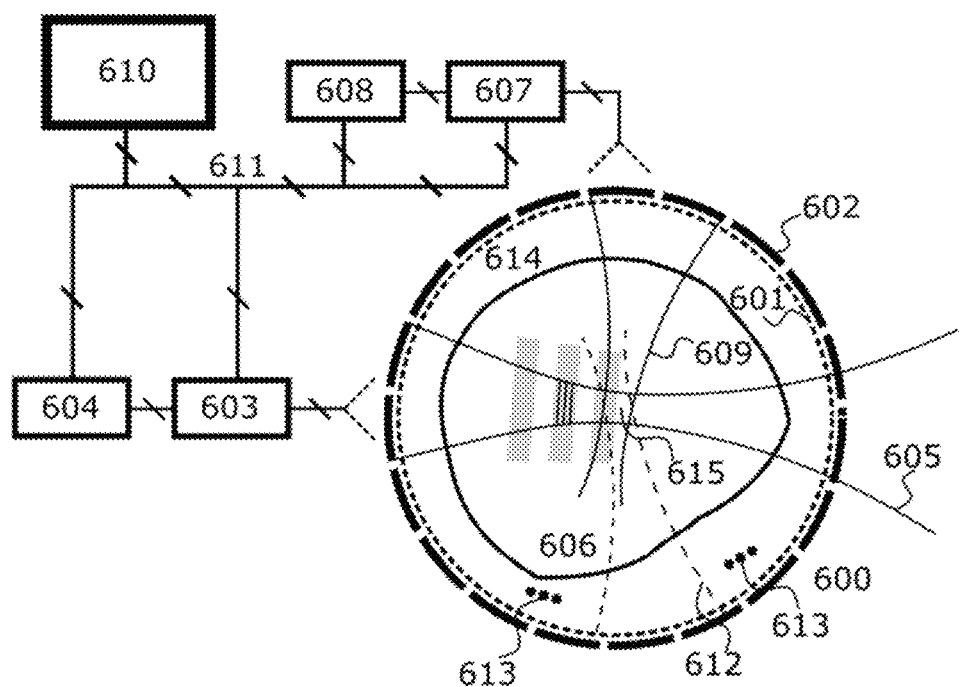
FIG. 6 shows a ring array transducer structure and processing system for estimation and imaging of linear and nonlinear nonlinear propagation and scattering parameters according to the invention.

The separate transmit and receive array systems in FIG. 2 can conveniently be substituted with a dual frequency ring array used for combined transmit and receive, shown as 600 in FIG. 6. The ring array surrounds an object 606 that is in acoustic contact with the ring array through a substance 614, typically a fluid like water or an oil. The ring array structure allows through-transmission of the ultrasound, typically used for ultrasound tomography imaging of objects, such as the breast and the male testicles.

601 of FIG. 6 shows a set of HF transmit/receive elements and 602 shows a set of LF transmit elements of ring array 600, for example described in more detail in [5-7]. The HF and LF elements are connected to a transmit switching system 603, that selectively connects a group of HF and LF elements to a HF and LF transmit system 604 comprising a HF and LF transmit beam former to generate selectable and/or steerable HF and LF transmit beams, where 605 shows an example HF transmit beam through the object 606. The HF array elements are also connected to a HF receive switching system 607, that selectively connects a group of HF elements to a HF receive system 608 comprising a HF receive beam former, that generates selectable and/or steerable HF receive cross-beams, where 609 shows an example crossing the transmit beam 605 at the observation cell 615, and a receive processing system 610 as described in relation to FIG. 2a to present estimates of object linear and nonlinear propagation and scattering parameters.

612 shows a further example HF receive cross-beam that crosses the HF transmit beam at the same cross-beam observation cell 615 as the HF receive cross-beam 609 with a different direction, and hence obtains a different speckle pattern of the front part 304 HF cross-beam receive signal, than for the HF receive cross-beam 609, as discussed in relation to FIG. 3, 6, 7 above. To obtain several HF receive cross-beams at different directions for each image point, indicated by the dots 613, the HF receive switching system connects selectable groups of HF array elements to the HF receive system 608 that produces a selectable number of HF cross-beam receive signals with different speckle of the front part 304, from selectable HF receive cross-beams in parallel. The variation in speckle in these different HF cross-beam receive signals from the same image point r allows for statistical averaging in the signal processing to reduce random errors in the estimates of the nonlinear propagation and scattering parameters. The subunits 603, 604, 607, 608 are connected to a processor and display system 610 via the bus 611 for set up, transmission, processing, and display of image data, according to known methods. The transmit 604 and receive 608 systems can alternatively be connected to all HF elements, and multiple transmit and receive beams are generated in parallel by for example a SW programmable system.

Because the modification of the bulk elasticity of the tissue by the LF pulse severely drops at the first scattering, as discussed following Eq.(13), the methods according to the invention as described above, do not require through-transmission through the object. A full ring array is therefore not necessary for these methods, where one for example could operate with a "horse-shoe" array extraction of the ring array 600 to emulate the functional essence of the array system in FIG. 2. A 360 deg ring array would however open for more measurements, such as direct transmission through the object, that can be used to improve spatial resolution and estimation accuracy of the NPD and PFD, using tomographic techniques. Such a ring array can also be used for tomographic estimation of local tissue absorption and linear propagation velocity according to known methods [13-17], that can be combined with methods according to this invention for improved detection and characterization of disease in tissue, as discussed in relation to Eqs.(28-37) below.

We further notice that measurement of through transmission of the HF pulses with a ring array can also be used to improve accuracy of estimates of the nonlinear propagation and scattering parameters with tomographic methods, where for example the values obtained according to the methods described above could be used as starting values in an iterative tomographic procedure, e.g. the "bent ray" method described in [13-17], to obtain more accurate values.

Figure 7A:
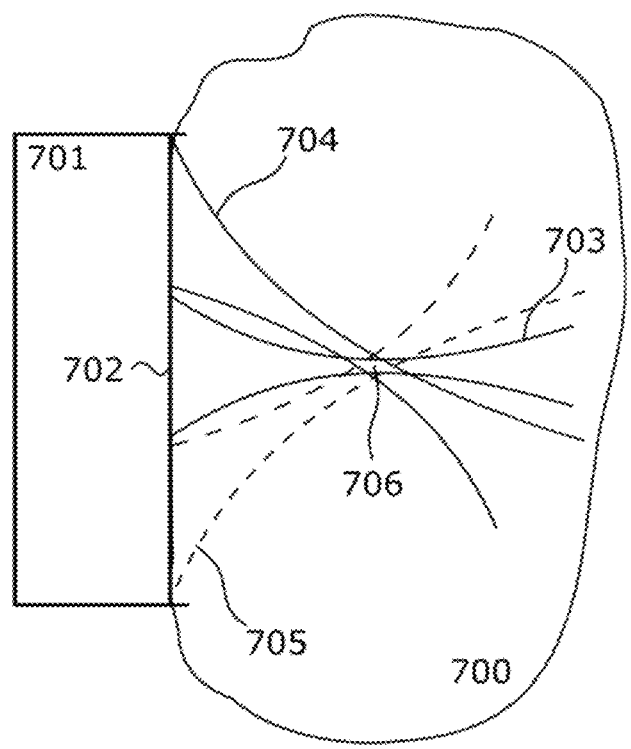
FIGS. 7a and b show yet two other example ultrasound transducer systems for estimation and imaging of linear and nonlinear propagation and scattering parameters according to the invention.

An example structure for assessment of nonlinear propagation and scattering parameters using a limited access area of the object, is shown in FIG. 7a, where 701 shows an array probe arrangement that is in direct contact with only one side of the object 700, for example the surface of a body. The probe front comprises a combined LF and HF array, 702, where selectable elements are used to transmit LF and HF pulse complexes, where 703 shows an example, schematic HF transmit beam. HF receive elements are selected from the array elements to define HF receive cross-beams, where an example, schematic HF receive cross-beam is shown as 704. 705 shows another example, schematic HF receive cross-beam crossing the HF transmit beam at the same cross-beam observation cell 706 as 704 at a different cross-angle, to obtain a HF receive signals with different speckle, for the same purpose as described for the beam 612 in FIG. 6. Through selection of one or both of i) transmit and receive array elements, and ii) transmit and receive delays, both the HF transmit and receive beams can according to known methods be scanned one or both of i) laterally along the probe surface, and ii) angularly from a given selection of elements, to generate crossing HF transmit and receive beams and move the cross-beam observation cell 706 within a region of the object, for estimation of linear and nonlinear object parameters using methods as described in relation to FIG. 2.

Figure 7B:
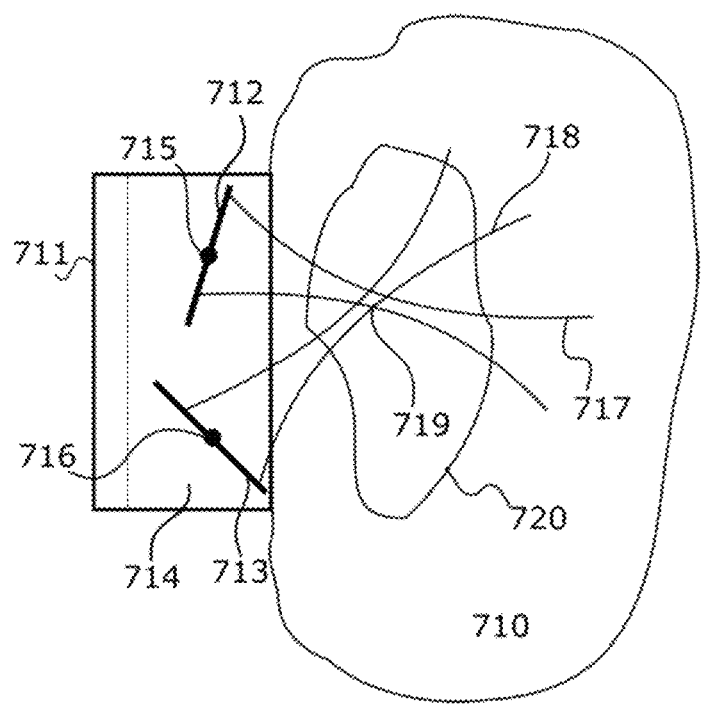

The strong angular steering of the HF transmit and receive beams in FIG. 7a requires down to $\lambda_{HF}/2$ pitch of the HF array, which increases the required number of elements. FIG. 7b shows a modification that allows the use of wider pitch of the elements, and also the use of annular arrays and even fixed focus transducers, to estimate linear and nonlinear wave propagation and scattering parameters in a cross-beam observation cell 719 of the object 710. 711 shows a combined transmit and receive system that comprises a LF and HF transmit array 712 and a HF receive array 713, embedded in a fluid filled region 714 to provide wave propagation contact to the object. Embedment in the fluid allows mechanical rotation of the arrays around the axes 715 and 716, or other mechanical movement of the arrays, potentially in combination with electronic scanning of the beam directions according to known methods. The LF-HF transmit array is connected to a transmit beam former inside the system 711 where an example resulting HF transmit beam is shown schematically as 717. The HF receive array 713 is connected to a HF receive beam former inside 711 that is used to define HF receive beams, for example schematically as 718, and further connected to a receive processing system according to the methods described in relation to FIG. 2. The beam formers and processing structures operates and are implemented according to known methods, and details are therefore not shown in the Figure. The system allows crossing HF transmit and receive beams with an overlap 719 that defines the transmit-receive cross-beam observation cell 719 that can be scanned within a region of the object, exemplified with 720, by scanning the receive and/or the transmit beams as described for 211 in relation to FIG. 2 and to Eqs.(16-25).

The coupling medium 714 between the transmit and receive arrays (712, 713) and the object allows the transmit and receive arrays to have an angle to the object surface, which hence allows for larger pitch of the array elements. With linear arrays one can scan the transmit and receive beams side-ways for imaging of linear and nonlinear propagation and scattering parameters as presented in relation to FIG. 2. Mounting the transmit and receive arrays 712 and 713 to rotating shafts 715 and 716, respectively, allows mechanical scanning of the transmit and receive beams that enlarges the number of measurement observation regions that can be obtained. The arrays 712 and 713 can then be reduced to annular arrays with sharp symmetric focusing, and even fixed focused transducers for a limited number of cross beam observation regions. Mechanical scanning of the beams in an elevation direction (normal to the paper plane) also opens for 3D imaging of regions of the object with methods according to this invention. These solutions also allow for low cost systems for estimation of linear and nonlinear propagation and scattering parameters in selected regions of an object.

The system according FIG. 7b can conveniently be simplified for objects that are approximately homogenous, such as the muscle of a fish or even a human, to measure for example uniform fat content in the muscle. One then can use fixed directions of fixed focused annular transmit and HF receive arrays (712, 713) that provides a fixed cross-beam observation region. From the measured NPD one can estimate the nonlinear propagation factor as $$\beta_{pa} \approx \frac{\tau(\text{cell}) - \tau(0)}{T(\text{tissue}) p_c} \quad (27)$$

$$T(\text{tissue}) = (T(\text{cell}) - T(\text{surface}))/2$$

where $\tau(\text{cell})$ is the measured NPD at the cross-beam observation cell 719, $\tau(0)$ is a previously measured NPD from the transmit array 712 through the acoustic contact medium 714 to the surface of the object, and T(tissue) is the propagation time from the probe surface to the center of the cross-beam observation cell. The composition of the homogeneous tissue can then for example be obtained from a table of prior data.

We note that the direct measurement of the effect of nonlinear elasticity parameter $\hat{\beta}_{pa}$ as in Eqs.(20-22) produces a result that according to Eqs.(1-11) depend on both the direct nonlinear elasticity parameter B(r) and the compressibility $\kappa=1/A$. When we have an estimate of $\kappa(r)$ we note from Eqs.(4-11) that we can estimate the pure nonlinear elasticity term B(r) from the estimate $\hat{\beta}_{pa}(r)$ in Eqs.(20-22, 27) as $$\hat{B}(\underline{r}) = \frac{2}{\hat{\kappa}}\left(\frac{\hat{\beta}_{pa}}{\hat{\kappa}} - 1\right) \quad (28)$$

where the hat denotes estimates. This introduces a pure nonlinear elasticity parameter with less correlation to the linear parameter $A(\underline{r})=1/\kappa(\underline{r})$ and $c_0(\underline{r})$. However, the effect of B on the nonlinear elasticity is also determined by how much the material compresses from a given pressure, that makes $B/A=B\kappa$ a better description of the relative effect of nonlinear elasticity on wave propagation, as described following Eq.(1). With the further development to the wave equation, Eqs.(7,9), we note that it is the slowly varying component $\beta_{pa}=(1+B_a\kappa_a/2)\kappa_a$ that affects the forward wave propagation and determines the NPD and the PFD. This is one reason that Ballou found a high correlation between B/A and $c_0$ [11].

When estimates of $c_0(\underline{r})$ exist, for example from ultrasound tomography or other, one can also obtain estimates of the nonlinear elasticity parameters B/A and B defined in Eqs.(1-4). One can for example use an empirical relation $\kappa=\kappa(c_0)$, or for example an approximate linear correlation between the mass density and the isentropic compressibility as [16]

$$\hat{\rho} \approx b - a\kappa \approx 1362 - 0.81 \cdot 10^{12}\kappa \quad (29)$$

$$\kappa = 1/\rho c_0^2$$

$$\hat{\kappa} \approx \frac{b - \sqrt{b^2 - 4a/c_0^2}}{2a} \approx \frac{1362 - \sqrt{1362^2 - 4 \cdot 0.81 \cdot 10^{12}/c_0^2}}{2 \cdot 0.81 \cdot 10^{12}}$$

Within this approximation one can hence obtain estimates of both the local mass density and the local compressibility of the tissue from $c_0(\underline{r})$. One could also use more complex parametric models of the relationship between mass density and isentropic compressibility.

The high correlation between $\beta_{pa}$ and $\kappa_a$ can also be used to generate estimates $\hat{c}_0(\underline{r})$, for example as $$\hat{c}_0(\hat{\beta}_{pa}) \approx \frac{1}{\sqrt{(b - a\hat{\kappa}(\hat{\beta}_{pa}))\hat{\kappa}(\hat{\beta}_{pa})}} \quad (30)$$

where $\hat{\kappa}(\hat{\beta}_{pa})$ is an empirical relation between $\hat{\beta}_{pa}$ and $\hat{\kappa}$. Eq.(30) then implies that $\hat{c}_0$ itself could be directly obtained from an empirical relation between $\hat{\beta}_{pa}$ and $\hat{c}_0$, for example as shown in FIG. 10. Such estimates for $\hat{c}_o$ could be used as initial values for iterative improvement procedures of estimates of $c_0(\underline{r})$, for example to form start parameters in iterative "bent ray" estimation procedures to estimate the spatially varying linear wave propagation velocity and absorption, for example according to tomographic methods [13-17].

When a first image of $c_0(\underline{r}_{ij})$ is estimated, one can use these values to estimate corrections for wave front aberrations in the heterogeneous medium for both the transmit and the receive beams [8,9]. We describe two methods for estimation of corrections for wave front aberrations for focusing the transmit and/or receive beams from an array aperture $S_{rf}$ onto the focal point $\underline{r}_f$. We assume $S_{rf}$ comprises a set of K elements out of the total number of elements in the array, where $\underline{r}_k$ is the center of array element #k. We first by example do spatial interpolation of $c_0(\underline{r}_{ij})$ to $c_0(\underline{r})$ with an adequately low spatial sampling distance.

In the first method we start by numerical simulation of the wave propagation from a point source in the focal point at $\underline{r}_f$ to the actual array aperture, through the heterogeneous object with spatially varying propagation velocity $c_0(\underline{r})$. We write the simulated wave function at the center $\underline{r}_k$ of array element #k as $g(\underline{r}_k,\underline{r}_f,\omega)$, where $\omega$ is the angular frequency of the point source at the focal point $\underline{r}_f$. We note that $g(\underline{r}_k,\underline{r}_f,\omega)$ is the Greens function for the point source at $\underline{r}_f$. We then filter the transmit pulse for each element by the filter $$h(\underline{r}_k,\underline{r}_f,\omega) = a(\underline{r}_k,\underline{r}_f) g(\underline{r}_k,\underline{r}_f,\omega)^* \quad k=1,\ldots,k \tag{31}$$

where $A(\underline{r}_k,\underline{r}_f)$ is the standard amplitude apodization of the transmit pulse across the actual aperture $S_{rf}$. The phase of g represents both the standard focusing delay for beam forming in a homogeneous medium, and together with the amplitude of g an optimal correction for the wave front aberrations due to the spatially varying propagation velocity [8,9]. The major component of this filter is however the linear component of the phase that represents a delay correction for the wave front aberrations.

This first method requires a large numerical simulation capacity, which has a practical solution using Graphics Processing Units (GPUs). A less computer intensive approach can be obtained with ray acoustics techniques. We define $\bar{c}$ as the spatial average of $c_0(\underline{r})$ over the actual region in front of the array. The well-known differential equation for an acoustic ray $\underline{r}(s)$ that passes normal to the acoustic wave fronts, is given in [18] as $$\frac{d}{ds}\left(n\frac{d\underline{r}}{ds}\right) = \nabla n \tag{32}$$

$$n(\underline{r}) = \frac{\bar{c}}{c_0(\underline{r})}$$

where s is the arc-length along the ray (i.e. $\underline{r}(s)$ is a taxameter representation of the ray) and $n(\underline{r})$ is the spatially varying refractive index of the material. To focus the transmit or receive beams onto the focal point $\underline{r}_f$, we simulate numerically Eq.(32) for the acoustic ray $\underline{r}_{fk}(s)$ from the focal point $\underline{r}_f$ to the center $\underline{r}_k$ of array element #k. The beam steering delay for element #k is then calculated as $$\tau_f(\underline{r}_k, \underline{r}_f) = \frac{1}{\bar{c}}[al(\underline{r}_k, \underline{r}_f) - al(\underline{r}_0, \underline{r}_f)] \tag{33}$$

$$al(\underline{r}_k, \underline{r}_f) = \int_{\underline{r}_{fk}} ds\, n(\underline{r})$$

$$k = 1,\ldots,K$$

where $al(\underline{r}_k,\underline{r}_f)$ is the acoustic length of the acoustic ray $\underline{r}_{fk}(s)$ from $\underline{r}_f$ to $\underline{r}_k$.

For best results one should do 3D scanning of the beams to obtain 3D images of $c_0(\underline{r}_{ij})$ as described above. For corrections of wave front aberrations, the array should with mechanical elevation scanning be of the 1.75D type with larger elements in the elevation direction used for beam focusing and aberration corrections. With a full matrix array, one obtains electronic focusing and beam steering both in the azimuth and elevation directions. For stationary objects the aberration corrections can be included in the filter functions $W(\omega,\underline{r}-\underline{r}_0,\underline{r})$ of Eqs.(18,19) for synthetic focusing of the observed beams. Hence with mechanical scanning in the elevation direction, we can avoid dividing of the arrays in the elevation direction, as focusing in the elevation direction can be done in the synthetic focusing.

We note that the NPD and the PFD estimated with the crossing transmit and receive beams can also be used in the processing of back-scattered HF signals obtained with a HF receive beam axis along or close to the HF transmit beam axis, as for example described in U.S. Pat. Nos. 7,641,613, 8,038,616, 8,550,998, 9,291,493 to suppress multiple scattering noise and estimate nonlinear scattering for received HF back-scatter signals. The back scatter images have better spatial resolution in range, and is also the type of images currently in general use, while the cross beam method provides more accurate estimation of the spatial variation of the NPD and PFD with less influence from multiple scattering noise.

It is in many aspects interesting to also form images from HF back-scatter receive signals using HF receive beams with the same axis as the HF transmit beams. This is obtained by a HF back-scatter receive beam forming on the HF receive array channel data, in addition to the HF receive cross-beam forming. The NPD and the PFDs are determined by the LF and HF transmit beams and the LF pulse polarity and the amplitude, according to Eqs.(12,13). When we for HF back-scatter receive signals are using the same LF and HF transmit beams as for the cross-beam receive signals, we get the same NPD and PFD for the HF back-scatter as for the cross-beam receive signals. The HF back-scatter receive signals can then be processed for suppression of multiple scattering noise and enhancement of nonlinear scattering signals, for example as described in U.S. Pat. Nos. 7,641, 613, 8,038,616, 8,550,998, 9,291,493. For each HF back-scatter receive beams we estimate from the NPD and PFD one or both of i) time delay corrections, and ii) pulse form and speckle corrections, for the at least two HF back-scatter receive signals from at least two transmitted pulse complexes with different LF pulses, followed by combinations of the corrected HF back-scatter receive signals to produce HF back-scatter receive signals with suppression of multiple scattering noise. Special delay and speckle corrections can similarly be estimated for enhancement of HF nonlinear scattering signals, for example as described in U.S. Pat. No. 9,291,493.

It is shown in U.S. Pat. No. 9,291,493 that Class I and II multiple scattering noise are equal for equal transmit and receive beams, which is a great advantage for combined suppression of both noise classes, as described in the cited US patent. For back-scatter imaging it is hence an advantage to form receive beams that are equal to the transmit beams, i.e. same focus, aperture, and apodization. This, however, gives fixed focused beams, but synthetic depth focusing of the combined transmit/receive beam can be obtained by lateral filtering of the received HF back-scatter receive signals as in Eqs.(34-37) and also U.S. Pat. No. 9,291,493.

A useful method is therefore to couple the array elements to a receive beam former that produces both receive cross-beams that crosses the transmit beams like in in FIGS. 2, 6, 7a, and 7b, and HF back-scatter receive beams close to equal to the HF transmit beams. The HF cross-beam receive signals are used for estimation of at least the spatially varying NPD, $\tau_p(\underline{r})$, as described above, and potentially also the PFD filter $\tilde{V}_p(\underline{r},\omega)$, the $\beta_{pa}(\underline{r})$, the $c_0(\underline{r})$, the $H(\underline{r}_k,\underline{r}_f)$, and the $\tau_f(\underline{r}_k,\underline{r}_f)$ as described in Eqs.(18-33) above. The spatially varying PFDs and/or the NPDs obtained from the cross-beam signals are then used to estimate correction of the HF back-scatter signals from equal HF transmit and HF backscatter receive beams for efficient suppression of the multiple scattering noise, as for example described in U.S. Pat. No. 9,291,493.

The HF back-scattered receive signals can be synthetically focused at multiple depths through lateral filtering as one of before and after the suppression of the MSN, for example as described in Eqs.(34-37) and U.S. Pat. No. 9,291,493. Estimation of $H(\underline{r}_k,\underline{r}_f)$, and the $\tau_f(\underline{r}_k,\underline{r}_f)$ from the cross beam signals as described in Eqs.(31-33) above, also allows for correction for the wave front aberrations in the synthetic focus filtering of Eqs.(18, 19, 34-37), according to known methods.

With the advances in compact computer storage and processing performance, the invention also devices a method for combined HF cross-beam and back-scatter imaging where the HF receive signals for the individual HF array elements are digitized and stored for each transmit pulse complex and each transmit beam. The stored receive element signals are then first processed to i) generate focused HF receive beams crossing the HF transmit beams for example as shown in FIGS. 2, 6, 7a, and 7b, according to known methods. The receive HF cross-beam signals are then used for estimation of at least the spatially varying NPD, $\tau_p(\underline{r})$, and potentially also the PFD $\tilde{V}_p(\underline{r},\omega)$, as described above, and further $\beta_{pa}(\underline{r})$, the $\hat{c}_0(\underline{r})$, the $H(\underline{r}_k,\underline{r}_f)$, and the $\tau_f(\underline{r}_k,\underline{r}_f)$ as described in Eqs.(20-24) and Eqs.(29-33) above.

In further steps, the method applies further processing on the stored element signals to ii) form a set of HF back-scatter receive signals from HF receive back-scatter beams with axis along or close to the HF transmit beam axis and aperture, focus, and apodization that are equal to that of the HF transmit beams, and iii) The HF back-scatter receive signal contains multiple scattering noise that can be strongly suppressed by delay corrections and potentially also speckle and pulse form corrections of the HF back-scatter receive signals, and combining the corrected HF back-scatter signals from transmitted pulse complexes with different LF pulses as described in U.S. Pat. Nos. 8,038,616, 8,550,998, 9,291,493, to produce noise suppressed HF back scatter receive signals. Similar processing to suppress linear scattering and enhance nonlinearly scattered signals can also be done according to the cited patents.

iv) perform synthetic dynamic focusing of the noise suppressed HF back-scatter receive signals and the nonlinearly scattered signals by lateral filtering of the HF back-scatter receive signals at selected depths similar to Eqs.(18, 19, 34-37). Estimated $H(\underline{r}_k,\underline{r}_f)$ or $\tau_f(\underline{r}_k,\underline{r}_f)$ for example according to Eqs.(31,33) under point i) then allows correction of the wave front aberrations in the lateral filtering.

With such scanning of the HF transmit and receive beams in a 2D or 3D manner, the methods hence allow formation of 2D and 3D back-scatter images with suppression of multiple scattering noise and enhancement of nonlinear scattering and also with focus corrections for the wave front aberration effect from spatial variations in ultrasound propagation velocity.

As described above, the strong angular steering of the HF transmit and receive beams used for cross-beam estimation of the NPD as in FIG. 7a, requires down to $\lambda_{HF}/2$ pitch of the HF array, which increases the required number of elements. The LF is so low (e.g. ~500 kHz) that it is feasible to obtain $\Delta_{LF}/2$ pitch for the LF array, while $\lambda_{HF}/2$ pitch of the HF array can require undesirable large number of HF elements. A larger HF pitch could be allowed by using an angled HF transmit beam, for example as 704, at a low frequency, say at the lower end of the effective frequency band of the HF array, and utilizing for processing a harmonic component of the received signal at the upper end of the effective frequency band of the array with a direct forward HF receive beam, for example as 703. The direct forward receive beam sets weaker requirements on the pitch of the HF array, for example ~1.5 times the harmonic wavelength in the tissue. Lateral filtering of the received HF harmonic signal for many lateral HF receive beams, can then provide a HF receive beam with focus within a large range of depths. This gives a narrower receive beam that provides improved estimates of the PFD and/or NPD with strong suppression of effects from multiple scattering noise on the estimates, both from the cross-beam effect and the harmonic suppression of multiple scattering noise in the receive signal. The estimated PFD and/or NPD can also be used for increased suppression of multiple scattering noise and enhancement of nonlinear scattering in the received harmonic signal.

The NPDs and the PFDs at the different image points depend on both the transmitted LF amplitude and transmit LF/HF beam directions. From the estimated NPDs from an angled HF transmit beam and a forward HF receive beam at an harmonic band, we can estimate $\beta_p$ at a set of image points as described in relation to Eqs.(20-22). From the formula for the NPD, $\tau_p(\underline{r})$, in Eq.(12), or from a complete simulation of Eq.(9a,b), one can then obtain estimates of a new set of NPDs at the image points for LF pulses and beams with different direction and amplitudes, for example direct forward LF and HF transmit beams. The complete simulation also produces estimates of the PFD at the selected image points. For adequately stationary objects one can then use such estimated PFDs and/or NPDs for new HF back-scatter receive signals obtained with forward HF transmit beams with the same HF back-scatter receive beams as the HF transmit beams, to suppress multiple scattering noise and enhance nonlinear scattered signal for these HF back-scatter receive signals, similar to what described above and in U.S. Pat. No. 9,291,493. One can then obtain synthetic focusing with lateral filtering of the processed HF back-scatter receive signals with suppression of multiple scattering noise and enhancement of nonlinear scattering, also with compensation for wave front aberrations, as described above.

Figure 8:
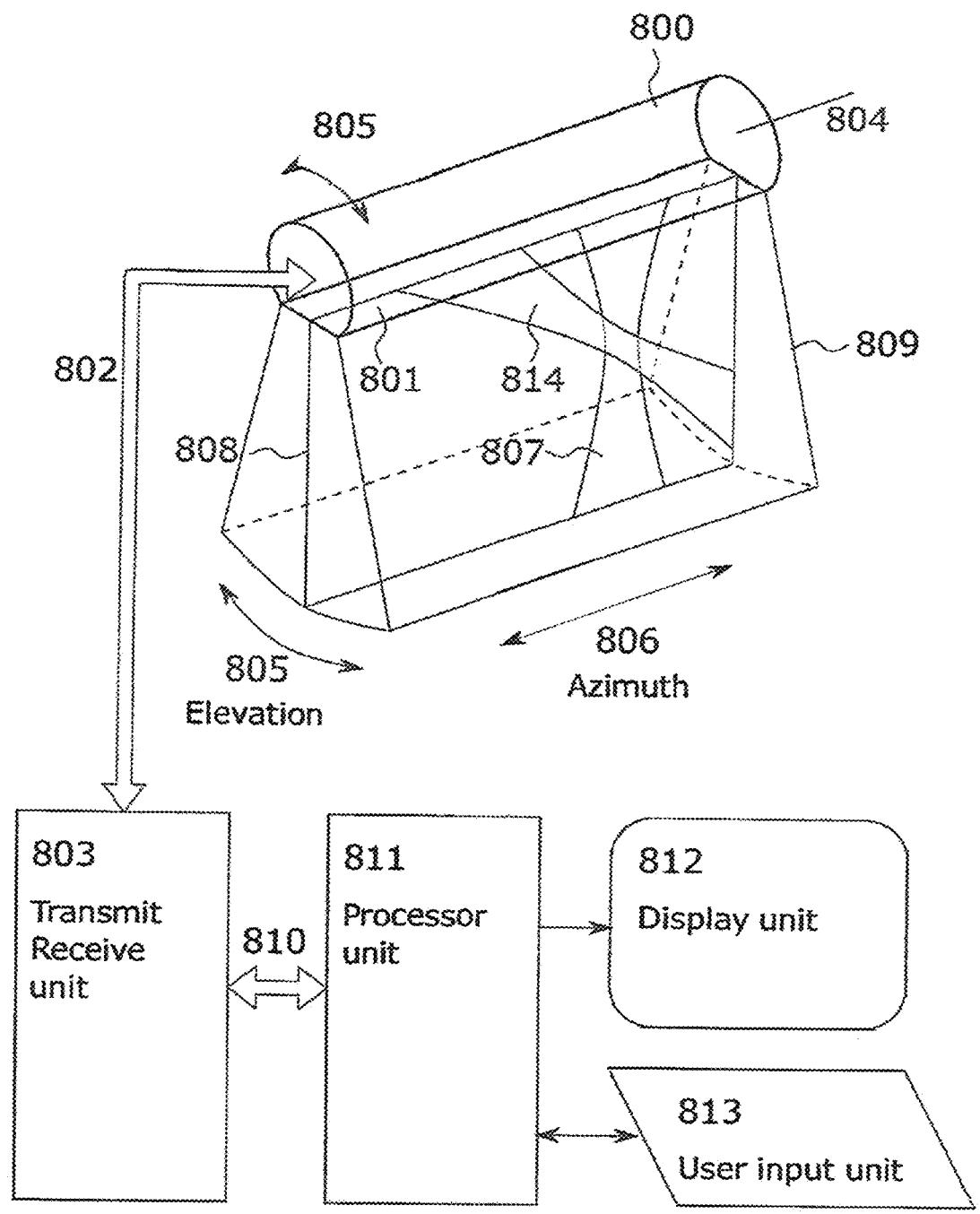
FIG. 8 shows a block diagram for an instrument according to the invention.

FIG. 8 shows a block diagram of an example instrument for carrying out imaging according to this method. 800 shows a 3D ultrasound probe comprising a dual frequency linear array 801 with a set of M LF elements and N HF elements in an azimuth direction indicated by the arrows 806. The dual frequency band linear array can be made according to known methods, for example as described in U.S. Pat. No. 7,727,156 [5]. The LF and HF elements of the array are via a cable 802 connected to a transmit/receive unit 803 that connects each LF array element to LF transmit amplifiers, and each HF element to HF transmit/receive circuits comprising a HF transmit amplifier and a HF receive amplifier where the output of the HF receive amplifier is further connected to an analog to digital converter (A/D) presenting a digital representation of the HF received signals from all HF receive elements, according to known methods. The AD converter can in a modified embodiment present digital representations of the I-Q components of the HF receive signals from each HF element that represents the same information as the radio frequency (RF) HF signal, according to known methods.

For 3D scanning of the ultrasound beams, the linear array 801 can in this example embodiment be rotated around the long axis 804 that provides a mechanical scanning of the LF/HF beam in an elevation direction, indicated by the arrows 805. For each elevation position of the array, one does electronic scanning of a combined LF/HF transmit beam in an azimuth direction indicated by the arrows 806, through electronic selection of transmitting LF and HF elements, and transmitting combined LF/HF pulse complexes similar to what is shown in FIG. 1, with selected beam directions and focus. An example HF transmit beam is illustrated schematically as 807 within a 2D azimuth plane 808 with given elevation position within a total 3D scan volume 809. Alternative elevation movements of the array, like side-ways movement can equivalently be done according to known methods, depending on the space available for such movement, and the shape of the object.

At least two pulse complexes with different LF pulses, for example as illustrated in FIG. 1, are transmitted for each transmit beam direction. The LF pulse might be zero in one pulse complex per HF transmit beam, but must be non/zero in at least one pulse complex for each HF transmit beam.

Two versions of the instrument are useful, where in the first version 803 comprises beam former for HF receive cross-beams, illustrated as 814 in the 2D scan plane 808, and HF back scatter receive beams with the same axis as the HF transmit beam 807. In a preferred embodiment the HF back-scatter receive beam is equal to the HF transmit beam as this improves suppression of multiple scattering noise in the HF back-scatter receive signal, as discussed in U.S. Pat. No. 9,291,493. During the scan, the HF cross-beam and back-scatter receive signals are via the high speed bus 810 transferred to the processor 811 for storage and further processing.

The processor 811 comprises a multicore central processing unit (CPU) and a graphics processor unit (GPU) that are SW programmable. The processor receives user inputs from a user/operator input unit 813 that operates according to known methods, and displays image data and other information necessary for communication with the user/operator through a combined display and audio unit 812, according to known methods.

In the second version, the digital HF receive signals from each HF receive elements and each transmitted pulse complex are via the high speed bus 810 transferred to the processor 811 for storage and further processing. For 2D imaging in the second version, a SW program in the processor 811 combines HF receive signals from multiple HF receive elements and produces a set of HF receive cross-beams crossing each HF transmit beam in the 2D set, for example as described in relation to FIG. 7a. A SW program also produces a set of HF back-scatter receive signals from HF back-scatter receive beams with the same axis as the HF transmit beams, and preferably also equal to the HF transmit beams.

Figure 9:
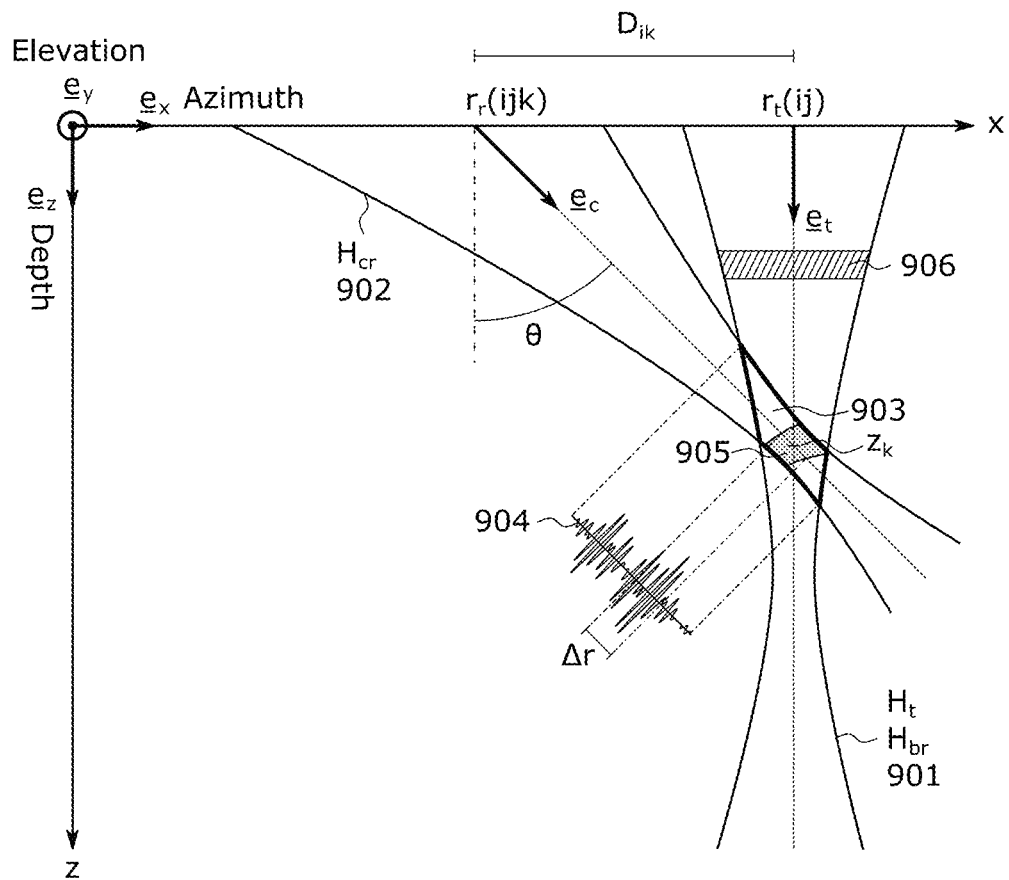
FIG. 9 shows schematically an HF transmit beam, an HF receive cross-beam, and a HF back-scatter receive beam equal to the HF transmit beam.

Example transmit and receive beams are shown in FIG. 9, where 901 shows by example a combined HF transmit beam, $H_t$, and HF back-scatter receive beam, $H_{br}$. The spatial frequency responses of the HF transmit beam and the HF back-scatter receive beam are $H_t(\underline{r}-\underline{r}_t,\omega)$ and $H_{br}(\underline{r}-\underline{r}_t,\omega)$. The position vector $\underline{r}_t(i,j)$ defines the origin of the HF transmit and receive beam axes, where i defines the azimuth aperture center element position, and j defines the 2D scan plane elevation position in a 3D scan. 902 shows an example HF receive cross-beam focused at the HF transmit beam axis at depth $z_k$, $H_{cr}(\underline{r}-\underline{r}_r,\omega)$, where $\underline{r}_r(i,j,k)$ defines the origin of the HF receive cross-beam axes, where i, j defines the azimuth and elevation position, and k defines the depth of the cross-over image point $z_k$ that is also the focus point of $H_{cr}$. 903 shows a cross-beam observation cell by the cross-over region between a HF transmit beam and the HF receive cross-beam, and 904 shows an indication of a HF cross beam receive signal from the whole cross-over region. By gating out a limited interval of this HF receive signal, the effective range of the observation cell is reduced along the cross-beam axis to the hatched region 905. A schematic form of the HF back-scatter observation cell is shown as the hatched region 906, along the HF combined transmit and back-scatter receive beams 901.

The dimensions of the observation cells can be reduced by filtering of the received signals, as shown in Eqs.(18,19). Estimates of the NPD and PFD can then be obtained from the HF cross-beam receive signals at several observation cells along each transmit beam, f.ex. as described in relation to FIG. 3 and Eq.(23). Estimates of the nonlinear propagation parameter and $\hat{\beta}_{pa}(\underline{r})p_c(\underline{r})$ and the quantitative propagation parameter $\hat{\beta}_{pa}(\underline{r})$ along the same HF transmit beam directions f.ex. according to Eqs.(20-22) or similar. This gives a 2D image of an estimate $\hat{\beta}_{pa}(\underline{r})$ within a 2D scan plane, indicated as 808. Using Eqs.(23-26) one can obtain a 2D cross-beam image of the linear and nonlinear scattering within the 2D scan plane. Display of the 2D image data are shown on the display unit 812.

Hence an adequate magnitude of the cross-angle between the HF transmit and receive beams produces suppression of the MSN in the HF cross-beam receive signal by i) directing the HF receive beams crossing the HF transmit beam at an adequately large cross-angle, and ii) focusing the HF receive cross-beams at the HF transmit beam axis, and iii) gating out HF receive signals from an interval of arrival times centered around the propagation time from the HF transmit beam axis. These three steps highly favors HF receive signals where the last scatterer is within a local HF cross-beam observation cell in the HF cross-over region around the cross-over depth between the HF transmit and receive beams axes, strongly suppressing MSN in this HF cross-beam receive signal, as MSN with arrival times within the gated HF receive interval must arrive from last scatterers outside said HF cross-over region which has low sensitivity.

To obtain HF cross-beam receive signals from a multitude of depths along the HF transmit beams one uses a set of parallel such HF receive cross-beams, that crosses the HF transmit beam at the depths one wants information from. The magnitude of suppression of HF cross-beam MSN compared to back scatter imaging depends amongst other on the cross-angle between the HF receive cross-beam and the HF transmit beam, in relation to the object structures that produces the MSN, and the type of arrays used. In medical ultrasound imaging the MSN is often given by large, plane fat-layers, parallel to a linear ultrasound transducer array. In this case one can get a ~6 dB suppression of the MSN with a cross-angle down to ~10 deg. A more robust suppression of the MSN for different situations is obtained if the cross-angle is typically larger than ~10 deg often larger than ~20 deg or even larger than ~30 deg, where the essence of the angle choice is to adequately suppress multiple scattering noise in the HF cross-beam receive signal for robust estimation of one or both of the NPD and the PFD.

When we have an estimate of the linear compressibility across the 2D scan plane, $\hat{\kappa}(\underline{r})=1/A(\underline{r})$, for example from other sources, we obtain a 2D image estimate of the nonlinear parameter $B(\underline{r})$ or $B(\underline{r})/A(\underline{r})$ from Eq.(28). When spatial estimates of the linear propagation velocity $c_0(\underline{r})$ exists, we can produce spatial estimates of the linear compressibility according to Eq.(29). Other estimates of the compressibility can be obtained from empirical correlation with the linear compressibility and $\hat{\beta}_{pa}(\underline{r})$, for example obtained by machine learning, which then could give estimates of $c_0(\underline{r})$ as in Eq.(30). This equation also gives direct empirical correlation between $\hat{\beta}_{Pa}(\underline{r})$ and the linear propagation velocity $c_0(\underline{r})$ as shown in FIG. 10.

From estimates of the linear propagation velocity, the processor can calculate corrections for wave front aberrations produced by the spatial variations in $c_0(\underline{r})$, for example according to Eqs.(31-33). These aberration correction estimates can then be included in the filter kernels of Eqs.(18, 19) to provide improved beam focusing with corrections for these aberrations, that reduces the dimension of the observation range cells. The processing on the element signals can then be carried through in several steps, where first a synthetic focusing of the HF receive beam and the HF transmit beam for the HF cross-beam receive signal according to Eqs.(18,19) are obtained with a spatially constant propagation velocity estimate, for example $c_0$=1540 m/s. This leads to a first estimate of a spatially varying $c_0(\underline{r})$ that opens for corrections for wave front aberrations in a second step, producing improved image estimates with lower dimension of the cross-beam observation cells. This leads to improved estimates of $c_0(\underline{r})$ that is used for improved corrections for wave front aberrations in a next step, leading to further improved image estimates with lower dimension of the cross-beam observation cells, and so on.

With the final estimate of $c_0(\underline{r})$, one can from Eqs.(31-33) calculate wave front aberration corrections for the combined HF transmit beam and the HF back-scatter receive beam. These corrections are then included in a lateral filtering of the HF back-scatter receive signals at selected depths, to provide synthetic focusing of the combined HF transmit and backscatter receive beams at said selected depths.

With 3D scanning of the beams we get 2D data from several neighboring 2D scan planes. Filters as in Eqs.(18,19) can now produce a 2D synthetic focusing of both the transmit and receive beams both in the azimuth and the elevation directions to minimize the observation cells at all depths along the transmit beams. The estimation of material data and images proceeds otherwise in the same manner as above for each 2D scan plane, to produce 3D images of material parameter estimates. The 3D synthetic focusing will produce smaller image cells with more accurate spatial estimates of the parameters, and improved corrections for wave front aberrations.

For good suppression of multiple scattering noise in the HF back-scatter receive signals, it is advantageous to use equal HF transmit and back-scatter receive beams, as described in U.S. Pat. No. 9,291,493. The HF back-scatter receive signal for an image pixel depth $z_k$=$ct_k$/2, where $t_k$ is the arrival time for the signal for that pixel, can be modeled as $$Y_p(z_k,\underline{r}_r,\omega)=U_p(z_k,\omega)\int d^2r_{t1}H_t(z_k,\underline{r}_r-\underline{r}_{t1},\omega)^2\sigma_p(z_k,\underline{r}_{t1},\omega) \quad (34)$$

where $H_tH_{br}=H_t^2$ because the HF back-scatter receive beam and transmit beams are equal. The back-scatter observation cell is defined by the HF pulse length in the z direction, and is hence short. A very useful synthetic focusing of the HF back-scatter receive signal can then be obtained by only transversal filtering of the HF back-scatter receive signal at fixed depth as $$\hat{Y}_p(z_k,\underline{r}_r,\omega)=U_p(z_k,\omega)\int d^2r_{t2}W_{rt}(z_k,\underline{r}_r-\underline{r}_{t2},\omega)Y_p(z_k,\underline{r}_{t2},\omega)$$

$$=U_p(z_k,\omega)\int z_1 d^2r_{t1}H_f(z_k,\underline{r}_r-\underline{r}_{t1},\omega)\sigma_p(z_k,\underline{r}_{t1},\omega)$$

$$H_f(z_k,\underline{r}_r,\omega)=\int d^2r_{t2}W_{rt}(z_k,\underline{r}_r-\underline{r}_{t2},\omega)H_t(z_k,\underline{r}_{t2},\omega)^2 \quad (35)$$

To minimize the width of $H_f$ in the transversal direction $\underline{r}_t$ we chose the filter kernel $W_{rt}$ so that the phase gradient of the Fourier transform $H_f$ in the transversal direction is zero [18]. Denoting the Fourier transform in the transversal coordinates by $F_{rt}\{\ \}$ the convolution gives $$F_{rt}\{H_f(z_k,\underline{r}_r,\omega)\}=F_{rt}\{W_{rt}(z_k,\underline{r}_r,\omega)\}F_{rt}\{H_t(z_k,\underline{r}_r,\omega)^2\}$$

$$F_{rt}\{W_{rt}(z_k,\underline{r}_r,\omega)\}=A_{rt}(z_k,\underline{k}_t,\omega)e^{-i\varphi_{rt}(z_k,\underline{k}_t)}\varphi_{rt}$$
$$(z_k,\underline{k}_t)=\varphi F_{rt}\{H_t(z_k,\underline{r}_r,\omega)^2\} \quad (36)$$

where $\underline{k}_t$ is the Fourier coordinates in the transversal plane, and Art is an apodization function to reduce sidelobes. In particular is the so-called matched filter $$F_{rt}\{W_{rt}(z_k,\underline{r}_r,\omega)\}=(F_{rt}\{H_t(z_k,\underline{r}_r,\omega)^2\})^* \quad (37)$$

useful, which includes both phase correction and apodization. Wave front aberrations can be included in our model of the HF transmit beam frequency response $H_t$ according to known methods, and the focus filtering in Eqs.(35-37) then also corrects for wave front aberrations.

For special versions of the processing one might also use all LF/HF array elements to transmit LF/HF beams that are approximately plane in the azimuth direction. Transmitting azimuth plane waves in several directions one can combine the received signals from the different directions to produce synthetic transmit beams focused at different locations within the 2D plane, according to known methods [4]. With a single azimuth direction azimuth plane wave, one can obtain spatial resolution with regular back-scatter registration of several parallel, dynamically focused receive beams, where time of arrival of scattered pulses produces spatial resolution along the depth of each receive beam, while the receive beam focusing produces lateral spatial resolution, all according to known methods. This method is however more sensitive to multiple scattering noise than the cross beam method described in relation to FIGS. 2, 6, and 7a, b.

The methods and instrumentation described above provides quantitative tissue images that opens for improved detection of tissue diseases, such as cancer and atherosclerotic plaques. It also opens for artificial intelligence (AI) detection and characterization of such diseases, when 3D data of the diseased tissue and some surrounding tissue is available.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps, which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed:

1. A method for estimation and imaging of propagation and scattering parameters in an object, comprising:
   transmitting at least two pulse complexes composed of an overlapping high frequency (HF) and a low frequency (LF) pulse along at least one LF and HF transmit beam axis, where said HF pulse propagates close to the crest or trough of the LF pulse, and where one or both of the amplitude and polarity of the LF pulse varies between the at least two transmitted pulse complexes, where the amplitude of the LF pulse can be zero for a pulse complex and the amplitude of the LF pulse for at least one pulse complex of said at least two transmitted pulse complexes is non-zero, and directing at least one HF receive cross-beam to cross said at least one HF transmit beam axis at a cross-angle to form cross-beam observation cells by overlap between each of said at least one HF receive cross-beam and each of said at least one HF transmit beam, and recording at least two HF cross-beam receive signals scattered from object structures in each cross-beam observation cell from said at least two transmitted pulse complexes with different LF pulses, and selecting the magnitude of said cross-angle to reduce multiple scattering noise in said HF cross-beam receive signals to produce adequately robust further processing of the HF cross-beam receive signals, and processing said HF cross-beam receive signals for each said at least one HF receive cross-beams to provide at least one of i) an estimated nonlinear propagation delay (NPD), and ii) an estimated nonlinear pulse form distortion (PFD), of the transmitted HF pulse at image points along said at least one HF transmit beam axis where said at least one HF transmit beam axis and said at least one HF receive cross-beam axis have shortest distance within each of said cross-beam observation cells, and using said estimated PFD and/or NPD for further processing, and gating out an interval of each said signals to form cross-beam receive signals scattered from cross-beam observation cells at different depths along each transmit beams to produce adequately robust further processing of the HF cross-beam receive signal.

2. The method according to claim 1, where said cross-angle is one of lager than 10 deg, 15 deg, 20 deg, 25 deg, 30 deg.

3. The method according to claim 1, where the processing of said HF cross-beam receive signals uses a harmonic component of the fundamental frequency band for said HF transmit pulse, to provide at least one of i) an estimated NPD, and ii) an estimated PFD.

4. The method according to claim 1, where said at least one HF receive cross-beam axis crosses the axis of said at least one HF transmit beam.

5. The method according to claim 4 where said at least one HF receive cross-beam is focused on the axis of said at least one HF transmit beam.

6. The method according to claim 1, further comprising directing for at least one image point more than one HF receive cross-beam that crosses said at least one HF transmit beam at different directions, with HF receive beam axes that crosses the HF transmit beam axes at essentially the same location close to an image point, and recording at least two scattered HF cross-beam receive signals for each said HF receive cross-beams scattered from the same pulse complexes with different LF pulses, and comparing said at least two scattered HF cross-beam receive signals for each said HF receive cross-beam, to estimate at least one of i) the NPD, and ii) the PFD, of the transmitted HF pulse, and combining said estimated PFD and/or NPD for each said HF receive cross-beams for said at least one image point, to form new estimated PFD and/or NPD with reduced estimation error for said image point, and using said new estimated PFD and/or NPD for further processing.

7. The method according to claim 1, further comprising receiving HF scattered cross-beam signals from the HF transmitted pulses for at least two image points along the HF transmit beam, and estimating an NPD for said at least two image points, and estimating and assigning to one of said image points at least one of i) a local nonlinear propagation parameter through combining the estimated NPD for said at least two image points, and ii) an average NPD of the transmitted HF pulse for said at least two image points.

8. The method according to claim 7, where said local nonlinear propagation parameter is scaled with an estimate of the LF pulse pressure at the location of the HF pulse at said each image point, to provide a quantitative estimate of the nonlinear propagation parameter $\beta_p$ at said each image point.

9. The method according to claim 1, further comprising:

transmitting said pulse complexes along a selected group of neighboring HF transmit beams, and receiving scattered HF cross-beam receive signals from the HF transmitted pulses for each of said neighboring HF transmit beams, where said selected group of HF transmit beams and HF receive cross-beams defines a selected group of image points, and combining in a filtering process the HF receive cross-beam signals from several of said selected group of image points to for at least one image point provide synthetically focused HF cross-beam receive signals produced by scatterers in a synthetically focused observation cell around said at least one image point, with reduced dimension compared to the original observation cell, and where said synthetically focused HF cross-beam receive signals are used in the further processing.

10. The method according to claim 1, further comprising:

correcting said at least two HF cross-beam receive signals with one or both of i) an estimated NPD, and ii) an estimated PFD, to produce at least two corrected HF cross-beam receive signals, and combining said at least two corrected HF cross-beam receive signals to form estimates of one or both of i) the nonlinearly scattered HF signal, and ii) the linearly scattered HF signal from at least one observation region.

11. The method according to claim 1, wherein said at least one HF transmit beam is scanned through a region of the object as one of i) across a 2D surface region, and ii) across a 3D region, and receiving for selected HF transmit beams within said region, HF cross-beam receive signals scattered from the HF transmitted pulse for at least two HF receive cross-beams with close distance along each selected HF transmit beam, and processing said HF receive signals to form one of both of 2D and 3D images at image points within said 2D and 3D region of at least one of i) an estimate of the NPD, and ii) an estimate of a nonlinear propagation parameter, and iii) a quantitative estimate of a nonlinear propagation parameter $\beta_p(\underline{r})$, and iv) an estimate of the linearly scattered signal, and v) an estimate of the nonlinearly scattered signal, at image points.

12. The method according to claim 11, where
for each selected group of HF transmit beams one uses HF receive beams equal to the HF transmit beams to receive at least two HF back-scatter receive signals from transmitted pulse complexes with different LF pulses, and
correcting said at least two HF back-scatter receive signals with at least one of i) an estimated NPD and ii) and estimated pulse form and speckle distortion, to provide at least two corrected HF back-scatter receive signals, and
combining said at least two corrected HF back-scatter receive signals to provide HF noise suppressed back-scatter receive signals with suppression of multiple scattering noise.

13. The method according to claim 12, where one of
i) said HF back-scatter receive signals are laterally filtered for synthetic focusing at selected depths before said correcting, and
ii) said HF back-scatter receive signals are laterally filtered for synthetic focusing at selected depths before said combining, and
iii) said HF noise suppressed back-scatter receive signals are laterally filtered for synthetic focusing at selected depths after said combining, to provide synthetically focused HF back-scatter receive signals with suppression of multiple scattering noise and focused at said selected depths.

14. The method according to claim 11, where said quantitative estimate of the spatially varying nonlinear propagation parameter $\beta_p(\underline{r})$ is used as input for at least one of
i) improved detection of abnormal tissue regions, and
ii) characterization of abnormal tissue regions, and
iii) estimating local changes in tissue properties during therapy, and
iv) estimating changes in local tissue temperature during therapy, and
v) estimating the spatially varying linear propagation velocity $c_0(\underline{r})$.

15. The method according to claim 1, where a selected group of said estimated parameters are used as starting values in an iterative procedure for tomographic reconstruction of tissue parameters with improved accuracy.

16. The method according to claim 1, where said estimated spatially varying propagation velocity $c_0(\underline{r})$ is used for estimation of aberration corrections of at least one of the at least one HF receive beams and the at least one HF transmit beams.

17. An instrument for carrying through the method according to claim 1, comprising
means for operator input/output for setting up the instrument components for a selected function,
transmit means for transmitting at least two pulse complexes composed of an overlapping high frequency (HF) and a low frequency (LF) pulse along at least one LF and HF transmit beam axis, where said HF pulse propagates close to the crest or trough of the LF pulse, and where one of the amplitude and polarity of the LF pulse varies between the at least two transmitted pulse complexes, where the amplitude of the LF pulse can be zero for a pulse complex and the amplitude of the LF pulse for at least one pulse complex of said at least two transmitted pulse complexes is non-zero, and
receive means for directing at least one HF receive cross-beam to cross said at least one HF transmit beam axis at a cross-angle to form cross-beam observation cells by the overlap between each of said at least one HF receive cross-beam and each of said at least one HF transmit beam, and
recording means for recording at least two HF cross-beam receive signals scattered from object structures in each cross-beam observation cell from said at least two transmitted pulse complexes with different LF pulses, where said cross-angle is selected at a magnitude to reduce multiple scattering noise in said HF cross-beam receive signals to produce adequately robust further processing of the HF cross-beam receive signals, and
processing means for processing said at least two HF cross-beam receive signals for each said at least one HF receive cross-beams to for at least one image point provide estimates of at least one of the parameters
i) an estimated nonlinear propagation delay (NPD), and
ii) an estimated nonlinear pulse form distortion (PFD), and
iii) an estimate of the linearly scattered signal with suppression of multiple scattering noise, and
iv) an estimate of the nonlinearly scattered signal with suppressions of linearly scattering components, and
v) an estimate of a spatially varying nonlinear propagation parameter, and
vi) an estimate of a spatially varying nonlinear propagation parameter $\beta_p(\underline{r})$, and
vii) an estimate of a spatially varying linear propagation velocity $c_0(\underline{r})$, and
viii) local estimates of the object mass density and the isentropic linear compressibility, and
ix) estimates of local changes in tissue properties during therapy, and
x) estimates of changes in local tissue temperature during therapy,
display means for display of images of said estimated parameters.

18. The instrument according to claim 17, where said processing means in the processing of said HF cross-beam receive signals uses a harmonic component of the fundamental frequency band for said HF transmit pulse, to provide at least one of i) an estimated NPD, and ii) an estimated PFD.

19. The instrument according to claim 17, further comprising
means for directing for at least one image point more than one HF receive cross-beam that crosses said at least one HF transmit beam at different directions, with HF receive beam axes that crosses the HF transmit beam axes at essentially the same location close to an image point, and
means for recording at least two scattered HF cross-beam receive signals for each said HF receive cross-beams scattered from the same pulse complexes with different LF pulses, and
means for comparing said at least two scattered HF cross-beam receive signals for each said HF receive cross-beams for said at least one image point, to estimate at least one of i) the NPD, and ii) the PFD, of the transmitted HF pulse for said at least one image point, and
means for combining said estimated PFD and/or NPD for each said HF receive cross-beams for said at least one image point, to form new estimated PFD and/or NPD with reduced estimation error for said at least one image point, and means for further processing of the HF receive signals utilizing said new estimated PFD and/or NPD to form estimates of said parameters.

20. The instrument according to claim 15, where
said transmit means transmits at least two pulse complexes along each of multiple HF transmit beam axes within one of a 2D and a 3D region of the object, and
said receive means and recording means receives and records HF cross-beam receive signals for multiple image points along each said multiple HF transmit beam axes, and
said processing means processes said at least two HF cross-beam receive signals scattered from pulse complexes with different LF pulses for each said multiple HF receive cross-beams, to provide estimates of at least one of said parameters at said multiple image points.

21. The instrument according to claim 20, where 2D scanning of the transmit beam and HF receive beams are obtained with an electronic array and beam-forming, while scanning in the elevation direction for 3D imaging is obtained with mechanical movement of the array.

22. The instrument according to any of claim 17 where said at least one HF receive cross-beam is focused close to an image point along the axis of a crossing HF transmit beam.

23. The instrument according to claim 17, where said transmitter means comprises an array of separate LF and HF elements and said receiver means comprises HF array elements that are selected within a selectable group of said HF transmit elements.

24. The instrument according to claim 17, where said transmitter means and said receiver means are arranged as separate units.

25. The instrument according to claim 24, where said array of LF and HF elements are arranged as a structure surrounding the object, and where said processing means is further arranged to estimate propagation and scattering parameters using tomographic methods.

26. The instrument according to claim 17, where said processing means is arranged to use estimates of nonlinear propagation and scattering parameters to establish initial values in an iterative tomographic procedure to estimate the spatially varying linear propagation velocity and spatially varying HF absorption in the object.

27. The instrument according to claim 26, where said processing means is organized to utilize the estimates of the spatially linear propagation velocity and HF absorption to obtain improved estimates of the nonlinear propagation and scattering parameters.

28. The instrument according to claim 17, where
said transmitter means comprises separate HF and LF transducer elements, and
said receiver means is set up to use the HF transducer elements to produce HF back-scatter receive beams that are co-aligned with the HF transmit beams with the same beam axes, in addition to said HF cross-over receive beams, and
said processor means is arranged to from one or both of said estimated NPD and PFD to estimate noise corrections for the HF back-scatter receive signals, and
said processor means is arranged to correct the HF back-scatter signals with said estimated noise corrections to produce corrected HF back-scattered signals, and said processor means is arranged to combine said corrected HF back-scattered signals to produce estimates of one or both of i) linear HF backscatter signal with suppression of multiple scattering noise, ii) nonlinear HF back-scatter signal with suppression of linear scattering signals.

29. The instrument according claim 20, where said HF transmit and said co-aligned HF back-scatter receive beams are scanned together in a 2D or 3D manner across a region of the object, to produce 2D or 3D back-scatter images of at least one of
i) linear HF back-scatter signal with suppression of multiple scattering noise, and
ii) nonlinear HF back-scatter signal with suppression of multiple scattering noise.

30. The instrument according to claim 28, where
said transmit and receive means are set up to produce equal HF transmit and HF back-scatter receive beams, and
said processor means is arranged to for a selection of depths to combine one of i) HF back-scatter receive signals, and ii) HF back-scatter receive signals with suppression of multiple scattering noise, for neighboring transmit-receive beams using differing weights of a focusing filter for each depth,
to provide synthetic focusing of the combined HF transmit and receive beams at said selection of depths for HF back-scatter receive signals with suppression of multiple scattering noise.

31. The instrument according to claim 17, where said processing means is set up to use said estimate of the linear propagation velocity $c_0(\underline{r})$ to estimate corrections for the wave front aberrations for at least one of i) the HF transmit beams, and ii) the HF receive beams.

32. The instrument according to claim 17, where said processing means is set up to adjust the weights of said focusing filter so that wave front aberration corrections are done in said focus filtering procedure.

33. The instrument according to claim 23, where
said HF transmit pulse is transmitted in a HF transmit band in the lower part of the electro-acoustic conversion band of said common array where said HF transmit beam axis has an angle to the array surface normal, and
said HF receive beam axis is close to the array surface normal, where
said HF recording means records a harmonic band of said HF fundamental transmit band for the scattered signal,
to provide at least one of i) an estimated NPD, and ii) an estimated PFD for different depths along said HF transmit beam.

34. The instrument according to claim 33, where
said NPD are stored for a set of multiple image points, and
a new set of at least two LF and HF pulse complexes are transmitted along a new set of HF transmit beams through said set of multiple image points, and
recording for each pulse complex HF back-scatter receive signals with HF receive beams equal to each HF transmit beams, and
estimating from said stored NPDs a set of at least one of i) delay and ii) speckle/pulse form corrections, and correcting said HF back-scatter receive signals with said set of speckle/pulse form and/or delay corrections to produce corrected HF receive signals, and
combining said corrected HF signals to form one or both of i) linear HF back-scatter receive signals with suppression of multiple scattering noise, and ii) nonlinear HF back-scatter receive signals with strong suppression of linear scattering signals.

35. The instrument according to claim 28, where
said receive means comprises separate electronic structures for generating said HF cross-beam receive signals, and said HF back-scatter receive signals, and
said HF cross-beam receive signals, and said HF back-scatter receive signals are transmitted to said processor means for further processing.

36. The instrument according to claim 28, where
the receive means comprises HF receive transducer elements at least in an azimuth direction, and the HF receive element signals are for all transmit beams and pulse complexes transferred to said processor means,
and said processor means comprises
i) a general programmable processor structure that allows processing of all HF receive beam forming and algorithms in software programs, and
ii) memory to store all necessary data, said software programs, and intermediate and final results of the processing.

* * * * *